US010478443B2

(12) United States Patent
El-Alfy et al.

(10) Patent No.: US 10,478,443 B2
(45) Date of Patent: Nov. 19, 2019

(54) SEX STEROID PRECURSORS ALONE OR IN COMBINATION WITH SELECTIVE ESTROGEN RECEPTOR MODULATORS FOR THE PREVENTION AND TREATMENT OF SEXUAL DYSFUNCTION IN POSTMENOPAUSAL WOMEN

(71) Applicant: ENDORECHERCHE, INC., Quebec (CA)

(72) Inventors: Mohamed El-Alfy, Quebec (CA); Fernand Labrie, Quebec (CA); Louise Berger, Quebec (CA)

(73) Assignee: ENDORECHERCHE, INC. (CA)

( * ) Notice: Subject to any disclaimer, the term of this patent is extended or adjusted under 35 U.S.C. 154(b) by 0 days.

(21) Appl. No.: 15/991,313

(22) Filed: May 29, 2018

(65) Prior Publication Data

US 2018/0271880 A1  Sep. 27, 2018

Related U.S. Application Data

(62) Division of application No. 14/464,536, filed on Aug. 20, 2014, now Pat. No. 10,076,525, which is a division of application No. 11/255,617, filed on Oct. 20, 2005, now Pat. No. 8,835,413.

(60) Provisional application No. 60/620,452, filed on Oct. 20, 2004.

(51) Int. Cl.
| | | |
|---|---|---|
| *A61K 31/5685* | (2006.01) | |
| *A61K 31/453* | (2006.01) | |
| *A61K 31/519* | (2006.01) | |
| *A61K 31/566* | (2006.01) | |

(52) U.S. Cl.
CPC ........ *A61K 31/5685* (2013.01); *A61K 31/453* (2013.01); *A61K 31/519* (2013.01); *A61K 31/566* (2013.01)

(58) Field of Classification Search
None
See application file for complete search history.

(56) References Cited

U.S. PATENT DOCUMENTS

| | | | |
|---|---|---|---|
| 4,789,669 A | 12/1988 | Sugimoto et al. | 514/178 |
| 5,246,704 A | 9/1993 | Sakaguchi et al. | 424/433 |
| 5,407,684 A | 4/1995 | Loria et al. | 424/442 |
| 5,629,303 A | 5/1997 | Labrie et al. | 348/716 |
| 5,728,688 A | 3/1998 | Labrie | 514/178 |
| 5,824,671 A | 10/1998 | Labrie | 514/178 |
| 5,834,451 A | 11/1998 | Ohsawa et al. | 514/177 |
| 5,840,735 A | 11/1998 | Labrie et al. | 514/320 |
| 6,007,824 A | 12/1999 | Druckett et al. | 424/195.1 |
| 6,013,665 A | 1/2000 | DeMichele et al. | 514/458 |
| 6,087,351 A | 7/2000 | Nyce | 514/178 |
| 6,087,362 A | 7/2000 | El-Rashidy | 514/253 |
| 6,294,550 B1 | 9/2001 | Place et al. | 514/253 |
| 6,340,480 B1 | 1/2002 | Druckett et al. | 424/728 |
| 6,465,445 B1 | 10/2002 | Labrie | 514/171 |
| 6,569,463 B2 | 5/2003 | Patel et al. | 424/497 |
| 6,583,129 B1 | 6/2003 | Mazer et al. | 514/167 |
| 6,670,346 B1 | 12/2003 | Labrie | 514/171 |
| 6,740,327 B2 | 5/2004 | Yu et al. | 424/401 |

(Continued)

FOREIGN PATENT DOCUMENTS

| | | |
|---|---|---|
| CA | 1320132 | 7/1993 |
| CA | 2154161 | 8/1994 |

(Continued)

OTHER PUBLICATIONS

Labrie, F et al: "Effect of 12-Month Dehydroepiandrosterone Replacement Therapy on Bone, Vagina, and Endometrium in Postmenopausal Women", Journal of Clinical Endocrinology and Metabolism, 1997, vol. 82, No. 10, pp. 3498-3505.

(Continued)

*Primary Examiner* — Sreenivasan Padmanabhan
*Assistant Examiner* — Jody L Karol
(74) *Attorney, Agent, or Firm* — Ostrolenk Faber LLP

(57) ABSTRACT

Novel methods for treating or reducing the likelihood of acquiring vaginal dysfunctions, more particularly vaginal dryness and dyspareunia, leading to sexual dysfunction and low sexual desire and performance, in susceptible warm-blooded animals including humans involving administration of a sex steroid precursor. Further administration of estrogen or selective estrogen receptor modulator, particularly those selected from the group consisting of Raloxifene, Arzoxifene, Tamoxifen, Droloxifene, Toremifene, Iodoxifene, GW 5638, TSE-424, ERA-923, and lasofoxifene, and more particularly compounds having the general structure:

is specifically disclosed for the medical treatment and/or inhibition of development of some of these above-mentioned diseases. Pharmaceutical compositions for delivery of active ingredient(s) and kit(s) useful to the invention are also disclosed.

4 Claims, 24 Drawing Sheets
(18 of 24 Drawing Sheet(s) Filed in Color)

(56) References Cited

U.S. PATENT DOCUMENTS

| | | |
|---|---|---|
| 6,824,786 B2 | 11/2004 | Yu et al. .................. 424/401 |
| 6,923,988 B2 | 8/2005 | Patel et al. ................ 424/489 |
| 7,045,513 B1 | 5/2006 | Parasrampuria et al. .... 514/170 |
| 7,226,910 B2 | 6/2007 | Wilson et al. ................ 514/12 |
| 8,835,413 B2 | 9/2014 | El-Alfy et al. ............. 514/178 |
| 10,076,525 B2* | 9/2018 | El-Alfy ............... A61K 31/453 |
| 2002/0013304 A1 | 1/2002 | Wilson et al. .............. 514/177 |
| 2002/0013327 A1 | 1/2002 | Lee ........................... 514/256 |
| 2002/0022052 A1 | 2/2002 | Dransfield ................. 424/449 |
| 2002/0032160 A1 | 3/2002 | Nyce ........................... 514/26 |
| 2002/0099003 A1 | 3/2002 | Wilson ......................... 514/2 |
| 2002/0107230 A1 | 8/2002 | Waldon et al. ............. 514/171 |
| 2002/0119936 A1 | 8/2002 | Nyce ........................... 514/26 |
| 2002/0128276 A1 | 9/2002 | Day et al. .................. 514/256 |
| 2002/0165429 A1 | 11/2002 | Thompson ................... 600/38 |
| 2002/0198136 A1 | 12/2002 | Mak ............................. 514/1 |
| 2002/0198179 A1 | 12/2002 | Labrie ........................ 514/102 |
| 2003/0022875 A1 | 1/2003 | Wilson et al. .............. 514/171 |
| 2003/0040510 A1 | 2/2003 | Labrie ........................ 514/171 |
| 2003/0065008 A1 | 4/2003 | Labrie ........................ 514/311 |
| 2003/0125319 A1 | 7/2003 | Day et al. .............. 514/217.06 |
| 2003/0130183 A1* | 7/2003 | Southard ............ A61K 9/0034 514/9.7 |
| 2003/0138434 A1 | 7/2003 | Campbell et al. ......... 424/184.1 |
| 2003/0181353 A1 | 9/2003 | Nyce ............................. 514/1 |
| 2003/0216329 A1 | 11/2003 | Robinson et al. ............ 514/26 |
| 2004/0014761 A1 | 1/2004 | Place et al. ................. 514/247 |
| 2004/0033963 A1 | 2/2004 | Yu et al. ...................... 514/23 |
| 2004/0044080 A1 | 3/2004 | Place et al. ................. 514/573 |
| 2004/0082522 A1 | 4/2004 | Nyce ........................... 514/26 |
| 2004/0092583 A1 | 5/2004 | Shanahan-Prendergast ............... 514/469 |
| 2004/0157812 A1 | 8/2004 | Labrie ........................ 514/177 |
| 2004/0180854 A1 | 9/2004 | Yu et al. ...................... 514/54 |
| 2004/0198706 A1 | 10/2004 | Carrara et al. .............. 514/169 |
| 2004/0219123 A1 | 11/2004 | Astruc et al. ............. 424/70.12 |
| 2005/0020552 A1 | 1/2005 | Aschkenasy et al. ........ 514/177 |
| 2005/0070487 A1 | 3/2005 | Nyce ........................... 514/26 |
| 2005/0070516 A1 | 3/2005 | Wilson et al. .............. 514/177 |
| 2005/0118272 A1 | 6/2005 | Besse et al. ................. 424/489 |
| 2005/0181057 A1 | 8/2005 | Rosenberg et al. .......... 424/488 |
| 2005/0215592 A1 | 9/2005 | Day et al. ................... 514/319 |
| 2005/0245494 A1 | 11/2005 | Thompson et al. .......... 514/171 |
| 2006/0018937 A1 | 1/2006 | Friedman et al. ............ 424/401 |
| 2006/0252734 A1 | 11/2006 | Woodward .................. 514/170 |
| 2006/0276442 A1 | 12/2006 | Woodward .................. 514/177 |
| 2007/0021360 A1 | 1/2007 | Nyce ........................... 514/44 |
| 2007/0042060 A1 | 2/2007 | Thompson .................. 424/742 |
| 2007/0253941 A1 | 11/2007 | Naidu ........................ 424/94.1 |
| 2007/0270394 A1 | 11/2007 | El-Alfy et al. ............. 514/178 |
| 2008/0090772 A1 | 4/2008 | Yu et al. ...................... 514/25 |
| 2008/0119445 A1 | 5/2008 | Woodward .................. 514/177 |
| 2008/0145418 A1 | 6/2008 | Zeligs ........................ 424/451 |
| 2008/0206161 A1 | 8/2008 | Tamarkin et al. ............. 424/45 |

FOREIGN PATENT DOCUMENTS

| | | |
|---|---|---|
| CA | 2334577 | 12/1999 |
| CA | 2515426 | 9/2004 |
| CA | 2584524 | 4/2006 |
| EP | 09792641 A1 | 9/1997 |
| EP | 0 802 183 A1 | 10/1997 |
| EP | 1199069 A2 | 4/2002 |
| EP | 1 623 712 A2 | 2/2006 |
| JP | 10036347 | 2/1998 |
| JP | 2002-179593 | 6/2002 |
| JP | 2002-517433 | 6/2002 |
| JP | 2003-212793 | 7/2003 |
| JP | 2003-520817 | 7/2003 |
| JP | 2003-527304 | 9/2003 |
| RU | 2004106024 | 4/2005 |
| WO | WO 90/010462 | 9/1990 |
| WO | WO 91/00731 | 1/1991 |
| WO | WO 91/00733 | 1/1991 |
| WO | WO 93/000070 | 1/1993 |
| WO | WO 94/16709 | 8/1994 |
| WO | WO 96/26201 | 8/1996 |
| WO | WO 97/25034 | 7/1997 |
| WO | WO 97/25035 | 7/1997 |
| WO | WO 97/25036 | 7/1997 |
| WO | WO 97/25037 | 7/1997 |
| WO | WO 97/25038 | 7/1997 |
| WO | WO 99/63973 | 12/1999 |
| WO | WO 99/63974 | 12/1999 |
| WO | WO 99/063974 | 12/1999 |
| WO | WO 00/002573 | 1/2000 |
| WO | WO 01/01969 | 1/2001 |
| WO | WO 01/54699 | 8/2001 |
| WO | WO 01/054699 | 8/2001 |
| WO | WO 2003/011243 | 2/2003 |
| WO | WO99/21562 | 7/2003 |
| WO | 2004/037262 A2 | 5/2004 |
| WO | WO2004/037262 A2 | 5/2004 |
| WO | WO 2005/066194 A1 | 7/2005 |
| WO | WO 2006/042409 | 4/2006 |
| WO | WO 2006/047859 A1 | 5/2006 |
| WO | WO 2006/133567 A1 | 12/2006 |
| WO | WO 2006/138686 A1 | 12/2006 |
| WO | WO 2009/021323 | 2/2009 |

OTHER PUBLICATIONS

Berger, L. et al.: "Effects of Dehydroepiandrosterone, Premarin and Acolbifene on Histomophology and Sex Steroid Receptors in the Rat Vagina", Journal of Steroid Biochemistry & Molecular Biology, 96 (Feb. 2005) 201-215.

Sourla, A. et al.: "Effect of Dehydroepiandrosterone on Vaginal and Uterine Histomorphology in the Rat" J. Steroid Biochem., 1998, vol. 66 (3), pp. 137-149.

Bachmann, G. et al.: "Diagnosis and Treatment of Atrophic Vaginitis", American Family Physician, 2000, vol. 61 (10), pp. 3090-3096.

Kim, N.N. et al., "Effects of Ovariectomy and Steroid Hormones on Vaginal Smooth Muscle Contractility", *Int J Impotence Res.*, (2004) 16:43-50.

Baulieu, Etienne-Emile et al., "Dehydroepiandrosterone (DHEA), DHEA Sulfate, and Aging: Contribution of the DHEAge Study to a Sociobiomedical Issue", *PNAS*, Apr. 11, 2000, vol. 97, No. 8, pp. 4279-4284.

Georges Pelletier, MD, PhD, et al.: "Androgenic Action of Dehydroepiandrosterone (DHEA) on Nerve Density in the Ovariectomized Rat Vagina," J Sex Med, 2013, vol. 10, pp. 1908-1914.

Fernand Labrie et al.: Corrigendum to "Effect of Intravaginal DHEA on Serum DHEA and Eleven of its Metabolites in Postmenopausal Women",[Journal of Steroid Biochemistry and Molecular Biology (2008) 178-194], Journal of Steroid Biochemistry & Molecular Biology, 2008, vol. 112, p. 169.

Propylene glycol—Wikipedia, 11 pages. Accessed Feb. 20, 2015.

Danielle D. Marshall, MD et al.: "A Guide to Lotions and Potions for Treating Vaginal Atrophy, Options for relieving the related itching, dryness, burning, and dyspareunia include a variety of hormonal formulations and nonhormonal alternatives," vol. 21, No. 12, Dec. 2009, OBG Management, pp. 29-37.

University of Maryland Medical center, "Dehydroepiandrosterone (DHEA)," Internet Article, [online] 2002, pp. 1-9, XP002506423, www.umm.edu/altmed/articles/dehydroepiandroesterone-dhea-000299.htm.

Extended European Search Report dated Jan. 15, 2009 in connection with the corresponding European application No. 05797148.3.

Casson et al., Delivery of dehydroepiandrosterone to premenopausal women: effects of micronization and nonoral administration. Am. J. Obstet. Gynecol., Feb. 1996, 174(2):649-53.

Christine Conrad, "A Woman's Guide to Natural Hormones" (2000) pp. 134-135.

Hardy, Ellen, "Women's Preferences for Vaginal Antimicrobial Contraceptives III" (1998) pp. 245-249.

(56) References Cited

OTHER PUBLICATIONS

Labrie et al., 2009, *Menopause: J. North American Menopause Society*, 16(5): 923-931.
Labrie et al., 2009, *Menopause: J. North American Menopause Society*, 16(5): 907-922.
Labrie et al., 2007, *J. Steroid Biochem. Mol. Biol.*, 107: 57-59.
Labrie et al., 2006, *J. Steroid Biochem. Mol. Biol.*, 99: 182-188.
Gauthier et al., 2008, *J. Med. Chemistry*, 40(14) 2116-2122.
Calvo et al., 2008, *J. Steroid Biochem. Mol. Biol.*, 112: 186-193.
Singh et al., 2000, *Current Med. Chemistry*, 7: 211-247.
Brzezinski et al., 2009, *Menopause: J. North American Menopause Society*, 16(5): 848-850.
Dubin et al., 1985, *Toxicology and Applied Pharmacology*, 78: 458-463.
Krogsgaard-Larsen et al., *Textbook of Drug Design and Dev.*, 154-155.
Dhareshwar et al., *Prodrugs of Alcohols and Phenols*, 3.2: 31-99.
Silverman, 1992, *Academic Press, Inc., The Org Chem of Drug Design and Drug Action*.
Belayet et al., 1999, *Human Reproduction*, 14(5): 1361-1367.
Maradny et al., 1996, *Human Reproduction*, 11(5): 1099-1104.
Yamashita et al., 1991, *U.S. Nat. Library of Med. Nat. Inst. Health*, 98(1): 31-9.
Glina et al., 2008, *J. Sex Med, Efficacy and Tolerability of Lodenafil* . . . .
Additional Options; vaginaldiscomfort.com, Accessed Oct. 20, 2009.
Is Perfume an Irritant?; sweetspotlabs.com, Accessed Oct. 20, 2009.
A search that refers to derivatives of acolbifene, Date of Search: Oct. 13, 2009.
Sourla et al., 1998, *J. Steroid Biochem. Mol. Biol.*, 66(3): 137-149.
Rossin-Amar, 2000, *Gynecol Ostet. Fertil.*, 28(3): 245-249.
Helzlsouer et al., 1992, *Cancer Res.*, 52(1): 1-4.
Szathmári et al., 1994, *Osteoporos. Int.*, 4(2): 84-88.
Thoman and Weigle, 1989, *Adv. Immununol.*, 46: 221-261.
Barrett-Connor et al., 1999, *J. Reprod. Med.*, 44(12): 1012-1020.
Barrett-Connor et al., 1999, *J. Am. Geriatr. Soc.*, 47 (96): 685-691.
Greendale and Judd, 1993, *J. Am. Geriatr. Soc.*, 41(4): 426-436.
Ross et al., 2000, *J. Natl. Cancer Inst.*, 92(4): 328-332.
Rosenberg et al., 1997, *J. Reprod. Med.*, 42(7): 394-404.
Burd et al., 2001, *Curr Women Health Rep.*, 1(3): 202-205.
Labrie et al., 2001, *Ref. Gyn, Obstet.*, 8: 317-322.
Lasco et al., 2001, *European Journal of Endocrinology*, 145: 457-461.
Gauthier et al., 1997, *J. Med. Chem.*, 40: 2117-2122.
Labrie et al., 1999, *J. Steroid Biochem. Mol. Biol.*, 69 (1-6) : 51-84.
Tremblay et al., 1998, *Endocrinology*, 139: 111-118.
Dauvois et al., 1991, *Cancer Res.*, 51: 3131-3135.
Luo et al., 1997, *Endocrinology*, 138: 4435-4444.
Willson et al., 1997, *Endocrinol.*, 138(9): 3901-3911.
Kramer, 1956, *Biometrics*, 12: 307-310.
Notelovitz, 2000, *Menopause*, 7(3): 140-142.
Berman et al., 1999, *Curr. Opin. Urol.*, 9(6): 563-568.
Labrie et al., 1996, *Endocrinol.*, 150: S107-S118.
Emmens and Martin, 1964, *Dorfman Ed, Ed Academic Press NY*:1.
Labrie et al., 2003, *Endocrinol.*, 144 (11): 4700-4706.
Anderson and Kang, 1975, *Am J anat*, 144(2): 197-207.
Yoshida et al., 1998, *Cancer Lett*, 134(1): 43-51.
Sourla et al., 1998, *Endocrinol.*, 139: 753-764.
Sourla et al., 2000, *J. Endocrinol.*, 166(2): 455-462.
Martel et al., 1998, *J. Endocrinol.*, 157: 433-442.
Knudsen and Mahesh, 1975, *Endocrinol.*, 97(2): 4580-468.
Lephart et al., 1989, *Biol. Reprod.*, 40(2): 259-267.
Shao et al., 1950, *J. Biol. Chem.*, 250: 3095-3100.
Poortman et al., 1975, *J. Clin. Endocrinol Metab.* 40(3): 373-379.
Van Doorn et al., 1981, *Endocrinol.*, 108: 1587-1594.
Adams et al., 1981, *Cancer Res.*, 41: 4720-4726.
Poulin and Labrie, 1986, *Cancer Res.*, 46: 4933-4937.
Martel et al., 2000, *J. Steroid Biochem. Mol. Biol.*, 74 (1-2): 45-56.
Munarriz et al., 2003, *J. Urol.* 170 (2 Pt. 2): S40-S44, Discussion S44-S-45.
Simoncini et al., 2002, *Endocrinol.*, 143(6): 2052-2061.
Guay and Jacobson, 2002, *J. Sex Marital Ther.*, 28 Suppl. 1:129-142.
Mattsson et al., 1989 *Maturitas*, 11:217-222.
Casson et al., 1997, *Obstet. Gynecol.*, 90(6): 995-998.
Hackenberg et al., *J. Steroid Biochem. Molec. Biol.*, vol. 46, No. 5, 1993, pp. 597-603.
Couillard et al., *Journal of the National Cancer Institute*, vol. 90, No. 10, May 20, 1998, pp. 772-778.
Luo et al., *Breast Cancer Research and Treatment*, 49:1-11, 1998.
Labrie et al., *Steroids*, 63:322-328, 1998.
Van Lingen, et al. *Multi-dose pharmacokinetics of rectally administered acetaminophen in term infants*, Clinical Pharmacology & Therapeutics, vol. 66, No. 5, Nov. 1999, pp. 509-515.
De Muynck, et al. *Rectal Mucosa Damage in Rabbits After Subchronical Application of Suppository Bases*, Pharmaceutical Research, vol. 8, No. 7, 1991, pp. 945-950.
Christine Conrad, *A Woman's Guide to Natural Hormones*, A Perigee Book published by The Berkely Publishing Company, May 2000, pp. XII, XIII, 66, 67, 80, 81, 82, 83, 134, 135, 144-147 (first page of Chapter 11), 156, 157, 198 and 199.
Allen, Loyd V Jr, Worthen Dennis B, and Mink Bill, Suppository bases and their characteristics, In Suppositories, Chapter 3 pp. 27-49, Published by the Pharmaceutical Press, London, UK, 2008.
Archer, D. F. (2007). Drospirenone-containing hormone therapy for postmenopausal women. Perspective on current data, J Reprod Med 52(2 Suppl): 159-64.
Ayton, R. A., G. M. Darling, et al. (1996), A comparative study of safety and efficacy of continuous low dose oestradiol released from a vaginal ring compared with conjugated equine oestrogen vaginal cream in the treatment of postmenopausal urogenital atrophy, Br J Obstet Gynaecol,103(4): 351-8.
Bachmann, G., R. A. Lobo, et al. (2008), Efficacy of low-dose estradiol vaginal tablets in the treatment of atrophic vaginitis: a randomized controlled trial, Obstet Gynecol_111(1): 67-76.
Bachmann, G. A., M. Notelovitz, et al. (1992), Long-term non-hormonal treatment of vagina dryness, J Clin Pract Sex 8.
Baker, V. L. and R. B. Jaffe (1996), Clinical uses of antiestrogens,Obstet Gynecol Surv_51: 45-59.
E.E. Baulieu, G. Thomas, S. Legrain, N. LaWou, M. Roger, B. Debuire, V. Faucounau, L. Girard, M.P. Hervy, F. Latour, M.e. Leaud, A. Mokrane, H. Pitti-Ferrandi, C. Trivalle, O. de Lacharriere, S. Nouveau, B. Rakoto-Arison, J.e. Souberbielle, J. Raison, Y. Le Bouc, A. Raynaud, X. Girerd and F. Forette, Dehydroepiandrosterone (DHEA), DHEA sulfate, and aging: contribution of the DHEAge Study to a sociobiomedical issue, *Proc.Natl. Acad. Sci. U.S.A.* 97 (2000), pp. 4279-4284.
Baxendale, P. M., M. J. Reed, et al. (1981), Inability of human endometrium or myometrium to aromatize androstenedione, *J. Steroid Biochem* 14(3): 305-6.
Belanger, B. Candas, A. Dupont, L. Cusan, P. Diamond, J.L. Gomez and F. Labrie, Changes in serum concentrations of conjugated and unconjugated steroids in 40- to 80 year-old men, J. *Clin. Endocrinol. Metab.* 79 (1994), pp. 1086-1090.
Belanger, G. Pelletier, F. Labrie, O. Barbier and S. Chouinard, Inactivation of androgens by UDP-glucuronosyltransferase enzymes in humans, *Trends Endocrinol. Metab.* 14 (2003), pp. 473-479.
Beral, V. (2003), Breast cancer and hormone-replacement therapy in the Million Women Study, Lancet 362(9382): 419-27.
Beral, V., D. Bull et al. (2005), Endometrial cancer and hormone-replacement therapy in the Million Women Study, Lancet 365(9470): 1543-51.
Bulun, S. E., Z. Lin, et al. (2005), Regulation of aromatase expression in estrogen-responsive breast and uterine disease: from bench to treatment.Pharmacol Rev 57(3):359-83.
J.E. Buster, P.R Casson, A.B. Straughn, D. Dale, E.S. Umstot, N. Chiamori and G.E. Abraham, Postmenopausal steroid replacement with micronized dehydroepiandrosterone: preliminary oral bioavailability and dose proportionalitystudies, Am. J. Obstet. Gynecol., 166 (1992), pp. 1163-1168 discussion 1168-1170. D.L.
Chlebowski, R T., S. L. Hendrix, et al. (2003), Influence of estrogen plus progestin on breast cancer and mammography in healthy

(56) References Cited

OTHER PUBLICATIONS postmenopausal women: the Women's Health Initiative Randomized Trial, Jama 289(24): 3243-53.
Coleman, E.H. Leiter and RW. Schwizer, Therapeutic effects of dehydroepiandrosterone (DHEA) in diabetic mice, Diabetes 31 (1982), pp. 830-833.
Colditz, G. A., K. M. Egn, et al. (1993), Hormone replacement therapy and riks of breast cancer: results from epidemiologic studies, Am. J. Obstet. Gynecol. 168: 1473-1480.
Collaborative Group on Hormonal Factors in Breast Cancer (1997), Breast cancer and hormone replacement therapy: collaborative reanalysis of data from 51 epidemiological studies of 52,705 women with breast cancer and 108,411 women without breast cancer, .Lancet 350(9084): 1047-59.
Corrao, G., A. Zambon, et al. (2008), Menopause hormone replacement therapy and cancer risk: an Italian record linkage investigation, Ann Oncol., 19(1): 150-5.
Coughlin, S. S., A. Giustozzi, et al. (2000), A meta-analysis of estrogen replacement therapy and risk of epithelial ovarian cancer, J Clin Epidemiol 53(4): 367-75.
Deutsch, S., R. Ossowski, et al. (1981), Comparison between degree of systemic absorption of vaginally and orally administered estrogens at different dose levels in postmenopausal women, Am J Obstet Gyneco., 39(8): 967-8.
Dew, J. E., B. G. Wren, et al. (2003), A cohort study of topical vaginal estrogen therapy in women previously treated for breast cancer, Climacteric_6(1): 45-52.
P. Diamond, 1. Cusan, J.L. Gomez, A. Belanger and F. Labrie, Metabolic effects of 12-month percutaneous DHEA replacement therapy in postmenopausal women, J. Endocrinol., 150 (1996), pp. 543-S50.
Dugal, R., K. Hesla, et al. (2000), Comparison of usefulness of estradiol vaginal tablets and estriol vagitories for treatment of vaginal atrophy, Acta Obstet Gynecol Scand 79(4): 293-7.
Englund, D. E. and E. D. Johansson (1978), Plasma levels of oestrone, oestradiol and gonadotrophins in postmenopausal women after oral and vaginal administration of conjugated equine oestrogens (Premarin), Br J Obstet Gynaecol., 85(12): 957-64.
Fallowfield, L. D. Cella, et al. (2004), Quality of life of postmenopausal women in the Arimidex Tamoxifen Alone or in Combination (ATAC) Adjuvant Breast Cancer Trial.J. Clin Oncol, 22(21): 4261-71.
Feeley, K. M. and M. Wells (2001), Hormone replacement therapy and the endometrium, J Clin Pathol54(6): 435-40.
Furuhjelm, M., E. Karlgren et al. (1980), Intravaginal administration of conjugated estrogens in premenopausal and postmenopausal women, .Int J Gynaecol Obstet, 17(4): 335-9.
Galhardo, C. L., J. M. Soares, Jr., et al. (2006), Estrogen effects on the vaginal pH, flora and cytology in late postmenopause after a long period without hormone therapy, Clin Exp Obstet Gyneco133(2): 85-9.
Gambrell, R. D., Jr., F. M. Massey, et al. (1980), Use of the progestogen challenge test to reduce the risk of endometrial cancer, Obstet Gynecol, 55(6): 732-8.
Garg, P. P., K. Kerlikowske, et al. (1998), Hormone replacement therapy and the risk of epithelial ovarian carcinoma: a meta-analysis, Obstet Gynecol, 92(3): 472-9.
Grady, D., T. Gebretsadik, et al. (1995), Hormone replacement therapy and endometrial cancer risk: a meta-analysis, Obstet Gynecol, 85(2): 304-13.
Gupta, P., B. Ozel, et al. (2008), The effect of transdermal and vaginal estrogen therapy on markers of postmenopausal estrogen status, Menopause 15(1): 94-7.
Holmberg, L. and H. Anderson (2004), HABITS (hormonal replacement therapy after breast cancer—is it safe?), a randomised comparison: trial stopped, Lancet 363(9407): 453-5.
Holmberg, L., O. E. Iversen, et al. (2008), Increased risk of recurrence after hormone replacement therapy in breast cancer survivors, J Natl Cancer Inst 100(7): 475-82.

Holmgren, P. A., M. Lindskog, et al. (1989), Vaginal rings for continuous low-dose release of oestradiol in the treatment of urogenital atrophy, Maturitas 11(1): 55-63.
Hulley, S. B. (2002), Noncardiovascular disease outcomes during 6.8 ears of hormone therapy: Heart and estrogen/progestin replacement study follow-up (HERS II), JAMA 288: 58-66.
Jick, S. S., A. M. Walker, et al. (1993), Estrogens, progesterone, and endometrial cancer, Epidemiology 4(1):20-4.
C.C. Johnston Jr., S.L. Hui, RM. Witt, R Appledorn, RS. Baker and C. Longcope, Early menopausal changes in bone mass and sex steroids, J. Clin. Endocrinol. Metab. 61 (1985), pp. 905-911.
D.W. Hum, A. Belanger, E. Levesque O. Barbier, M. Beaulieu, C. Albert, M. Vallee, C. Guillemette, A. Tchernof, D. Turgeon and S. Dubois, Characterization of UDP-glucuronosyltransferases active on steroid hormones, J. Steroid Biochem. Mol. BioI. 69 (1999), pp. 413-423.
H. Kawano, H. Yasue, A. Kitagawa, N. Hirai, T. Yoshida, H. Soejima, S. Miyamoto, M. Nakano and H.Ogawa, Dehydroepiandrosterone supplementation improves endothelial function and insulin sensitivity in men, J. Clin. Endocrinol. Metab. 88 (2003), pp. 3190-3195.
Kendall, A., M. Dowsett, et al. (2006), Caution: Vaginal estradiol appears to be contraindicated in postmenopausal women on adjuvant aromatase inhibitors, Ann Oncol 17(4): 584-7.
Kvorning, J.D.N. and H.K. Jensen (1986), Pharmaceutical development of lose-dose estradiol vagitories, International Workshop, Copenhagen.
F. Labrie Future perspectives of SERMs used alone and in combination with DHEA, Endocr. Relat. Cancer 13 (2006), pp. 335-355.
Labrie, F. (2007), Drug Insight: breast cancer prevention and tissue-targeted hormone replacement therapy, Nature Clinical Practice, Endocrinology & Metabolism, 3(8): 584593.
Labrie, F. A. Belanger, et al. (2007), Metabolism of DHEA in postmenopausal women following percutaneous administration, J. Steroid Biochem Mol Biol 103(2): 178-88.
Labrie, F., A. Belanger, et al. (2005), GnRH agonists in the treatment of prostate cancer, Endocrine Reviews 26(3): 361-379.
Labrie, F., A. Belanger, et al. (2007), Metabolism of DHEA in postmenopausal women following percutaneous administration, J Steroid Biochem Mol Bio., 103(2):178-88.
Labrie, F., L. Cusan, et al. (2008), Effect of Intravaginal DHEA on Serum DHEA and Eleven of its Metabolites in Postmenopausal Women, Journal Ster Biochem & Mol Biol: In press.
Labrie, F., L. Cusan, et al. (2008), Effect of One-Week Treatment with Vaginal Estrogen Preparations on Serum Estrogen Levels in Postmenopausal Women, Menopause In press.
Labrie, F. L. Cusan, et al. (2008), Changes in serum DHEA and eleven of its metabolites during 12-month percutaneous administration of DHEA, .J Steroid Biochem Mol Biol, 110(1-2):1-9.
Labrie, F., A. Dupont, et al. (1985), Complete androgen blockade for the treatment of prostate cancer. Important Advances in Oncology, V. T. de Vita, S. Hellman and S. A. Rosenberg. Philadelphia, J.B. Lippincott: 193-217.
F. Labrie, V. Luu-The, S.X. Lin, C. Labrie, J. Simard, R. Breton and A. Belanger, The key role of 17β-HSDs in sex steroid biology, Steroids, 62 (1997), pp. 148-158.
Labrie, V. Luu-The, S.-X. Lin, J. Simard, C. Labrie, M. EI-Alfy, G. Pelletier and A.Belanger, Intracrinology: role of the family of 17β-hydroxysteroid dehydrogenases in human physiology and disease, J. Mol. Endocrinol. 25 (2000), pp. 1-16.
Labrie, F., V. Luu-The, et al. (2005), Is DHEA a hormone? Starling Review.J Endocrinol, 187: 169-196.
Labrie, F., V. Luu-The, et al. (2006), Dehydroepiandrosterone (DHEA) is an anabolic steroid like dihydrotestosterone (DHT), the most potent natural androgen, and tetrahydrogestrinone (THG), J Steroid Biochem Mol Biol., 100(1-3): 52-8.
F. Labrie, J. Simard, V. Luu-The, A. Belanger, G. Pelletier, Y. Morel, F. Mebarki, R. Sanchez F. Durocher, C. Turgeon, Y. Labrie, E. Rheaume, c. Labrie and Y. Lachance, The 3β-hydroxysteroid dehydrogenase/isomerase gene family: lessons from type II 3β-HSD congenital deficiency. In: V. Hansson, F.O. Levy and K. Tasken,

(56) References Cited

OTHER PUBLICATIONS

Editors, Signal Transduction in Testicular Cells. Ernst Schering Research Foundation Workshop, vol Suppl. 2, Springer-Verlag, Berlin (1996), pp. 185-218.
Labrie, J. Simard V. Luu-The, A. Belanger and G. Pelletier, Structure, function and tissue-specific gene expression of 3β-hydroxysteroid dehydrogenase/5-ene-4-ene isomerase enzymes in classical and peripheral intracrine steroidogenic tissues, J. Steroid Biochem. Mol. Biol. 43 (1992), pp. 805-826.
F. Labrie, R. Poulin, J. Simard, V. Luu-The, C. Labrie and A. Belanger, Androgens, DHEA and breast cancer, In: T. Gelfand, Editor, Androgens and Reproductive Aging, Taylor and Francis, Oxsfordshire, UK (2006), pp. 113-135.
Labrie, Y. Sugimoto, V. Luu-The, J. Simard, Y. Lachance, D. Bachvarov, G. Leblanc, F. Durocher and N. Paquet, Structure of human type II 5α-reductase, Endocrinology, 131 (1992), pp. 1571-1573.
Y. Labrie F. Durocher, Y. Lachance, C. Turgeon J. Simard, C. Labrie and F. Labrie, The human type II 17β-hydroxysteroid dehydrogenase gene encodes two alternatively-spliced messenger RNA species, DNA Cell Biol. 14 (1995), pp. 849-861.
Lacey, J. V., P. J. Mink, et al. (2002), Menopausal hormone replacement therapy and risk of ovarian cancer, JAMA 288: 334-341.
Li, L., S. J. Plummer, et al. (2008), A common 8q24 variant and the risk of colon cancer: a population-based case-control study, Cancer Epidemiol Biomarkers Prev 17(2): 339-42.
C.H. Liu, G.A. Laughlin D.G. Fischer and S.S. Yen, Marked attenuation of ultradian and circadian rhythms of dehydroepiandrosterone in postmenopausal women: evidence for a reduced 17,20-desmolase enzymatic activity, ]. Clin. Endocrinol. Metab., 71 (1990), pp. 900-906.
Long, C. Y., C. M. Liu, et al. (2006), A randomized comparative study of the effects of oral and topical estrogen therapy on the vaginal vascularization and sexual function in hysterectomized postmenopausal women, Menopause 13(5): 737-43.
V. Luu-The, I. Dufort, N. Paquet, G. Reimnitz and F. Labrie, Structural characterization and expression of the human dehydroepiandrosterone sulfotransferase gene, DNA Cell. Biol. 14 (1995), pp. 511-518.
V. Luu-The, Y. Zhang, D. Poirier and F. Labrie, Characteristics of human types I, 2 and 3 17β-hydroxysteroid dehydrogenase activities: oxidation-reduction and inhibition, J Steroid Biochem. Mol. Biol., 55 (1995), pp. 581-558.
Lyytinen, H., E. Pukkala, et al. (2006), Breast cancer risk in postmenopausal women using estrogen-only therapy, Obstet Gyneco1108(6): 1354-60.
E.G. MacEwen and I.D. Kurzman, Obesity in the dog: role of the adrenal steroid dehydroepiandrosterone (DHEA), J. Nutr. 121 (1991), pp. S51-S55.
Mandel, F. P., F. L. Geola, et al. (1983), Biological effects of various doses of vaginally administered conjugated equine estrogens in postmenopausal women, J Clin Endocrinol Metab 57(1): 133-9.
Manonai, J., U. Theppisai, et al. (2001), The effect of estradiol vaginal tablet and conjugated estrogen cream on urogenital symptoms in postmenopausal women: a comparative study, J Obstet Gynaecol Res 27(5): 255-60.
Martin, P. L., S. S. Yen, et al. (1979), Systemic absorption and sustained effects of vaginal estrogen creams, Jama, 242(24): 2699-700.
Marx, P., G. Schade, et al. (2004), Low-dose (0.3 mg) synthetic conjugated estrogens A is effective for managing atrophic vaginitis, Maturitas, 47(1): 47-54.
R.B. Mazess, On aging bone loss, Clin. Orthop. 165 (1982), pp. 239-252.
Meisels, A. (1967), The maturation value, Acta Cyto111: 249.
Mertens, H. J., M. J. Heineman, et al. (1996), Androgen receptor content in human endometrium, Eur J Obstet Gynecol Reprod Biol 70(I): 11-3.
Mettler, L. and P. G. Olsen (1991), Long-term treatment of atrophic vaginitis with low-dose oestradiol vaginal tablets, Maturitas 14(1): 23-31.
C.J. Migeon, A.R. Keller, B. Lawrence and T.H. Shepart II., Dehydroepiandrosterone and androsterone levels in human plasma. Effect of age and sex: day-to-day and diurnal variations, J. Clin. Endocrinol. Metab. 17 (1957), pp. 1051-1062.
A.J. Morales, J-J. Nolan, J.C. Nelson and S.S Yen, Effects of replacement dose of dehydroepiandrosterone in men and women of advancing age, J. Clin. Endocrinol. Metab. 78 (1994), pp. 1360-1367.
Morales, L., P. Neven, et al. (2004), Acute effects of tamoxifen and third-generation aromatase inhibitors on menopausal symptoms of breast cancer patients, Anticancer Drugs 15(8): 753-60.
N.A.M.s. (2007), Position Statement of the North American Menopause Society, Menopause, 14: 357-69.
Nachtigall, L. E. (1995), Clinical trial of the estradiol vaginal ring in the U.S., Maturitas, 22 Suppl: 543-7.
Naessen, T., K. Rodriguez-Macias, et al. (2001), Serum lipid profile improved by ultra-low doses of 17 beta-estradiol in elderly women, J Clin Endocrinol Metab 86(6): 2757-62.
Nelson, H. D., K. K. Vesco, et al. (2006), Nonhormonal therapies for menopausal hot flashes: systematic review and meta-analysis, Jama 295(17): 2057-71.
J.E. Nestler, e.o. Barlascini, J.N. Clore and W.G. Blackard, Dehydroepiandrosterone reduces serum low density lipoprotein levels and body fat but does not alter insulin sensitivity in normal men, J. Clin. Endocrinol. Metab. 66 (1988), pp. 57-61.
Nilsson, K. and G. Heimer (1992), Low-dose oestradiol in the treatment of urogenital oestrogen deficiency—a pharmacokinetic and pharmacodynamic study, Maturitas 15(2): 121-7.
Notelovitz, M., S. Funk, et al. (2002), Estradiol absorption from vaginal tablets in postmenopausal women, Obstet Gynecol, 99(4): 556-62.
Orentreich, N., J. L. Brind, et al. (1984), Age changes and sex differences in serum dehydroepiandrosterone sulfate concentrations throughout adulthood, J. Clin. Endocrino!. Metab. 59: 551-555.
Persson, 1., H. O. Adami, et al. (1989), Risk of endometrial cancer after treatment with oestrogens alone or in conjunction with progestogens: results of a prospective study, Bmj 298(6667): 147-51.
Ponzone, R., N. Biglia, et al. (2005), Vaginal oestrogen therapy after breast cancer: is it safe?, Eur J Cancer 41(17): 2673-81.
Rigg, L. A., H. Hermann, et al. (1978), Absorption of estrogens from vaginal creams, N Engl J Med 298(4): 195-7.
B.L. Riggs, H.W. Wahner, W.L. Dunn, R.B. Mazess, K.P. Offord and L.J. Melton, Differential changes in bone mineral density of the appendicular and axial skeleton with aging: relationship to spinal osteoporosis, J. Clin. Invest. 67 (1981), pp. 328-335.
Riman, T., P. W. Dickman, et al. (2002), Hormone replacement therapy and the risk of invasive epithelial ovarian cacner in Swedish women, J Natl Cancer Inst 94: 497-504.
Rinaldi,S., H. Dechaud, et al. (2001), Reliability and validity of commercially available, direct radioimmunoassays for measurement of blood androgens and estrogens in postmenopausal women, Cancer Epidemiol Biomarkers Prev, 10(7): 757-65.
Rioux, J. E., C. Devlin, et al. (2000), 17beta-estradiol vaginal tablet versus conjugated equine estrogen vaginal cream to relieve menopausal atrophic vaginitis, Menopause 7(3): 156-61.
Rodriguez, C., A. V. Patel, et al. (2001), Estrogen replacement therapy and ovarian cancer mortality in a large prospective study of US women, JAMA 285: 1460-1465.
Rosenberg, L. V., C. Magnusson, et al. (2006), Menopausal hormone therapy and other breast cancer risk factors in relation to the risk of different histological subtypes of breast cancer: a case-control study, Breast Cancer Res 8(1): R11.
Salminen, H. S., M. E. Saaf, et al. (2007), The effect of transvaginal estradiol on bone in aged women: a randomised controlled trial, Maturitas 57(4): 370-81.
Schiff I., D. Tulchinsky, et al. (1977), Vaginal absorption of estrone and 17beta-estradiol, Fertil Steril, 28(10): 1063-6.

(56) References Cited

OTHER PUBLICATIONS

Schmidt, G., S. B. Andersson, et al. (1994) Release of 17-beta-oestradiol from a vaginal ring in postmenopausal women: pharmacokinetic evaluation, Gynecol Obstet Invest 38(4):253-60.

E.D. Schriock, C.K. Buffington, G.D. Hubert, B.R. Kurtz, A.E. Kitabchi, J.E. Buster and J.R. Givens, Divergent correlations of circulating dehydroepiandrosterone sulfate and testosterone with insulin levels and insulin receptor binding, J. Clin. Endocrinol. Metab. 66 (1988), pp. 1329-1331.

Sillero-Arenas, M., M. Delgado-Rodriguez, et al. (1992), Menopausal hormone replacement therapy and breast cancer: a meta-analysis.Obstet. Gynecol., 79: 286-294.

Simon, J. A., K Z. Reape, et al. (2007), Randomized, multicenter double-blind, placebo-controlled trial to evaluate the efficacy and safety of synthetic conjugated estrogens B for the treatment of vulvovaginal atrophy in healthy postmenopausal women, Fertil Steril. In press.

E.R Simpson, Role of aromatase in sex steroid action, J. Mol. Endocrinol., 25 (2000), pp. 149-156.

Simunic, V., 1. Banovic, et al. (2003), Local estrogen treatment in patients with urogenital symptoms, Int J Gynaecol Obstet 82(2): 187-97.

Smith, D.C., R Prentice, et al. (1975), Association of exogenous estrogen and endometrial carcinoma, N. Engl. J. Med. 293: 1164-1167.

Smith, P., G. Heimer, et al. (1993), Oestradiol-releasing vaginal ring for treatment of postmenopausal urogenital atrophy, Maturitas 16(2): 145-54.

Steinberg, K.K., S. B. Thacker, et al. (1991), A meta-analysis of the effect of estrogen replacement therapy on the risk of breast cancer, JAMA 265: 1985-1990.

K.K. Steinberg, L.W. Freni-Titulaer, E.G. DePuey, D.T. Miller, D.S. Sgoutas, C.H. Coralli, D.L. Phillips, T.N. Rogers and RV. Clark, Sex steroids and bone density in premenopausal and perimenopausal women, J. Clin. Endocrinol. Metab., 69 (1989), pp. 533-539.

Suckling, J., A. Lethaby, et al. (2006), Local oestrogen for vaginal atrophy in postmenopausal women, Cochrane Database System Rev 18(4): CD001500.

Swanson, M. Lorentzon, L. Vandenput, D. Mellstrom, F. Labrie, A. Rane, J. Jakobsson, C. Ohlsson, Sex Steroid Levels and Cortical Bone Size in Young Men Are Associated with a Uridine Diphosphate Glucuronoltransferase 2B7 Polymorphism ($H^{268}Y$), The Journal of Clinical Endocrinology & Metabolism, 92(9):3697-3704 (2007).

Tchernof, J.P. Despres, A. Belanger, A. Dupont, D. Prud'homme, S. Moorjani, P.J. Lupien and F. Labrie, Reduced testosterone and adrenal C19 steroid levels in obese men, Metabolism 44 (1995), pp. 513-519.

Turgeon, J.S. Carrier, E. Levesque, D.W. Hum and A. Belanger, Relative enzymatic activity, protein stability, and tissue distribution of human steroid-metabolizing UGT2B subfamily members, Endocrinology 142 (2001), pp. 778-787.

Utian, W. H., D. Shoupe, et al. (2001), Relief of vasomotor symptoms and vaginal atrophy with lower doses of conjugated equine estrogens and medroxyprogesterone acetate, Fertil Steril, 75(6): 1065-79.

Vermeulen and L. Verdonck, Radioimmunoassays of 17β-hydroxy-5*-androstan-3-one, 4-androstene-3,17-dione, dehydroepiandrosterone, 17β-hydroxyprogesterone and progesterone and its application to human male plasma, J. Steroid Biochem. 7 (1976), pp. 1-10.

D.T. Villareal and J.O. Holloszy, Effect of DHEA on abdominal fat and insulin action in elderly women and men: a randomized controlled trial, JAMA 292 (2004), pp. 2243-2248.

Voigt, L. F., N. S. Weiss, et al. (1991), Progestagen supplementation of exogenous oestrogens and risk of endometrial cancer, Lancet 338(8762): 274-7.

Weisberg, E., R. Ayton, et al. (2005), Endometrial and vaginal effects of low-dose estradiol delivered by vaginal ring or vaginal tablet, Climacteric 8(1): 83-92.

Wied, G. L. (1993), Industrial developments in automated cytology as submitted by their developers, Anal Quant Cytol Histol, 15(5): 358-70.

Wines, N. and E. Willsteed (2001), Menopause and the skin, Australas J Dermatol 42(3): 149-158; quiz 159.

Zang, H., L. Sahlin, et al. (2007), Effects of testosterone treatment on endometrial proliferation in postmenopausal women, J Clin Endocrinol Metab, 92(6): 2169-75.

B. Zumoff, C.W. Strain, L.K. Miller and W. Rosner, Twenty-four-hour mean plasma testosterone concentration declines with age in normal premenopausal women, J. Clin. Endocrinol. Metab. 80 (1995), pp. 1429-1430.

F. Labrie: "Dehydroepiandrosterone (DHEA) as Potential Hormone Replacement Therapy", Ref Gynecol Obstet, vol. 8, No. 5, Jan. 1, 2001, pp. 317,322.

F. Labrie, et al. High internal consistency and efficacy of intravaginal DHEA for vaginal atrophy, Gynelogical Endocrinology, Jul. 2010; 26(7): pp. 524-532.

Labrie et al., "Vaginal Atrophy High internal consistency and efficacy of intravaginal DHEA for vaginal atrophy," Gynecological Endocrinology, Jul. 2010; 26(7): 524-532.

Hatzimouratidis et al. Looking to the future for erectile dysfunction therapies, Drugs, 2008, 68(2):231-50.

EPO Communication dated Mar. 30, 2011 in Corresponding EP 05797148.3-2123.

Berman, Jennifer R., et al., "Effect of Estrogen Withdrawal on Nitric Oxide Synthase Expression and Opoptosis in the Rat Vagina," Urology, vol. 51, No. 4, Apr. 1998, pp. 650-656, 1998, Elsevier Science Inc.

Rosenthal, Ronnie A., et al., "Principles and Practice of Geriatric Surgery", 2001, Springer, ISBN: 978-0-38798393-6, p. 820.

Labrie, Ferngrid, et al., "EM-652 (SCH 57068), a third generation SERM acting as pure antiestrogen in the mammary gland and endometrium", Pergamon, Journal of Steroid Biochemistry and Molecular Biology, 69 (1999) 51-84.

Block, Lawrence H., Ph.D., "Medicated Topicals", Remington: The Science and Practice of Pharmacy, (2000), Chapter 44, pp. 836-857.

Rudnic, Edward M., Ph.D., et al, "Oral Solid Dosage Forms", Remington: The Science and Practice of Pharmacy, (2000) Chapter 45, pp. 858-893.

ACS Abstract—Han, Jeong Seon, et al, "Dissolution and rectal absorption of acetaminophen from suppositories" (1987), 31 (5), 286-95.

ACS Abstract—Guidici, Raymond A., et al, "Formulation and development of [a] neomycin-hydrocortisone suppository" (1979), 72, 13-16.

Shouqi Luo, et al., "Comparative Effects of 28-Day Treatment with the New Anti-Estrogen EM-800 and Tamoxifen on Estrogen-Sensitive Parameters in Intact Mice," Int. J. Cancer, vol. 73, pp. 381-391 (1997).

Céline Martel, et al., "Comparison of the Effects of the New Orally Active Antiestrogen EM-800 with ICI 182 780 and Toremifene on Estrogen-Sensitive Parameters in the Ovariectomized Mouse," Endocrinology, vol. 139, pp. 2486-2492 (1998).

Roerio A. Lobo, M.D., et al., "Comparative Effects of Oral Esterified Estrogens with and without Methyltestosterone on Endocrine Profiles and Dimensions of Sexual Function in Postmenopausal Women with Hypoactive Sexual Desire," Fertility and Sterility, vol. 79, No. 6 (Jun. 2003).

Jennifer R. Berman, et al., "Effect of Estrogen Withdrawal on Nitric Oxide Synthase Expression and Apoptosis in the Rat Vagina," Urology, vol. 51, No. 4, pp. 650-656, Elsevier Science Inc. (Apr. 1998).

Ronnie A. Rosenthal, et al., "Principles and Practice of Geriatric Surgery", Springer, ISBN: 978-0-387-98393-6, p. 820 (2001).

Rossouw, J. E., G. L. Anderson, et al., "Risks and benefits of estrogen plus progestin in healthy postmenopausal women: principal results From the Women's Health Initiative randomized controlled trial," JAMA 288(3): 321-33 (2002).

Labrie, F., V. Luu-The, et al., "Endocrine and intracrine sources of androgens in women: inhibition of breast cancer and other roles of androgens and their precursor dehydroepiandrosterone." Endocrine Reviews 24(2): 152-182 (2003).

(56) References Cited

OTHER PUBLICATIONS

Loyd V, Allen, et al., "Suppository Bases and Their Characteristics," Suppositories, pp. 27-49 (2008).
SciFinder® Wecobee, 19. Jeong Seon Han, et al., "Dissolution and rectal absorption of acetaminophen from suppositories," American Chemical Society (2012). 22. Raymond A. Giudici, et al., Formulation and development of [a] neomycin-hydrocortisone suppository, American Chemical Society (2012).
Claude Labrie et al.: Stimulation of Androgen-Dependent Gene Expression by the Adrenal Precursors Dehydroepiandrosterone and Androstenedione in the Rat Ventral Prostate, *Endocrinology*, vol. 124, No. 6, pp. 2745-2754, 1989.
Sasol—Product Information, WITEPSOL® and MASSA ESTARINUM®, Jan. 6, 2007 (2 total pages).
Michael W. Jann, Pharm. D., FCP, FCCP, et al., "Relative Bioavailability of Ondansetron 8-mg Oral Tablets Versus Two Extemporaneous 16-mg Suppositories: Formulation and Gender Differences," Pharmacotherapy, vol. 18, No. 2, pp. 288-294 (1998).
FATTIBASE™, Fatty Acid Suppository Base, Look to Paddock for All of Your Compounding Needs, Paddock Laboratories, Inc. (2010) (2 total pages).
Sasol brochure, Excipients for pharmaceuticals, Jul. 2010.
Suppository Bases, The Pharmaceutics and Compounding Laboratory, https://pharmlabs.unc.edu/labs/suppository/bases.htm, 1996.
Opposition against corresponding Ecuadorian Patent Application SP 2010-10016 filed by Asociacion de Laboratorios Farmaceuticos ("ALAFAR" by its Spanish acronym) (English language translation).
English language of a Search Report from the Patent Office of Georgia dated Jun. 2, 2008 in Application No. AP 2005 010069.
Jean Coope: "Hormonal and non-hormonal interventions for menopause symptoms", Maturitas, 23 (1996), pp. 159-168.
H. Hong et al: "Comparative molecular field analysis (CoMFA) model using a large diverse set of natural, synthetic and environmental chemicals for binding to the androgen receptor", SAR and QSAR in Environmental Research, 14:5-6, 373-388, DOI: 10.1080/10629360310001623962, (2003).

Fernand Labrie et al.: "Effect of toremifene and ospemifene, compared to acolbifene, on estrogen-sensitive parameters in rat and human uterine tissue", Horm Mol Giol Clin Invest 2010; 1(3): 139-146 (2010).
JoAnn V. Pinkerton et al: "Clinical effects of selective estrogen receptor modulators on vulvar and vaginal atrophy", Menopause: The Journal of the North American Menopause Society, vol. 21, No. 3, pp. 309-319, (2014) DOI: 10.1097/gme.0B013E31829755ed.
Fernand Labrie: Chapter 6: "Androgens in postmenopausal women: the practically exclusive intracrine formation and inactivation in peripheral tissues", *Section 2: The Scientific Essentials*, pp. 64-73 (2015).
Helen Singer Kaplan et al: "The Female Androgen Deficiency Syndrome", Journal of Sex & Marital Therapy, vol. 19, No. 1 (Spring 1993), ISSN: 0092-623X (Print) 1521-0715 (Online) Journal homepage http://www.tandfonline.com/loi/usmt20.
Xiao-Ning Wang et al.: "Lasofoxifene enhances vaginal mucus formation without causing hypertrophy and increases estrogen receptor β and androgen receptor in rats", Menopause: The Journal of the North American Menopause Society, vol. 13, No. 4, pp. 609-620 (2006).
H.Z. KE et al.: "Lasofoxifene (CP-336, 156), A Novel Selective Estrogen Receptor Modulator, in Preclinical Studies", J. Amer. Againg Assoc., vol. 25, pp. 87-100, (2002).
Pharmasave Health Library—"Be well Informed About Feminine Health Care" (accessed Nov. 19, 2009).
Pfizer for Professional CLEOCIN Vaginal Ovules (accessed Nov. 19, 2009; copyright, as shown on p. 4, 2009).
A. Yamashita, et al.: "Pharmacological studies of intravaginally applied dehydroepiandrosterone sulfate (DHA-S)", Nippon Yakurigaku Zasshi. Jul. 1991; 98(1):31-9 PMID: 1653759 [PubMed—Indexed for Medline] U.S. National Library of Medicine, National Institutes of Health, Abstract.
Irwin Goldstein, MD, et al.: "Practical Aspects in the Management of Vaginal Atrophy and Sexual Dysfunction in Perimenopausal and Postmenopausal Women", J Sex Med 2005; Supplement 3, pp. 154-165.

* cited by examiner

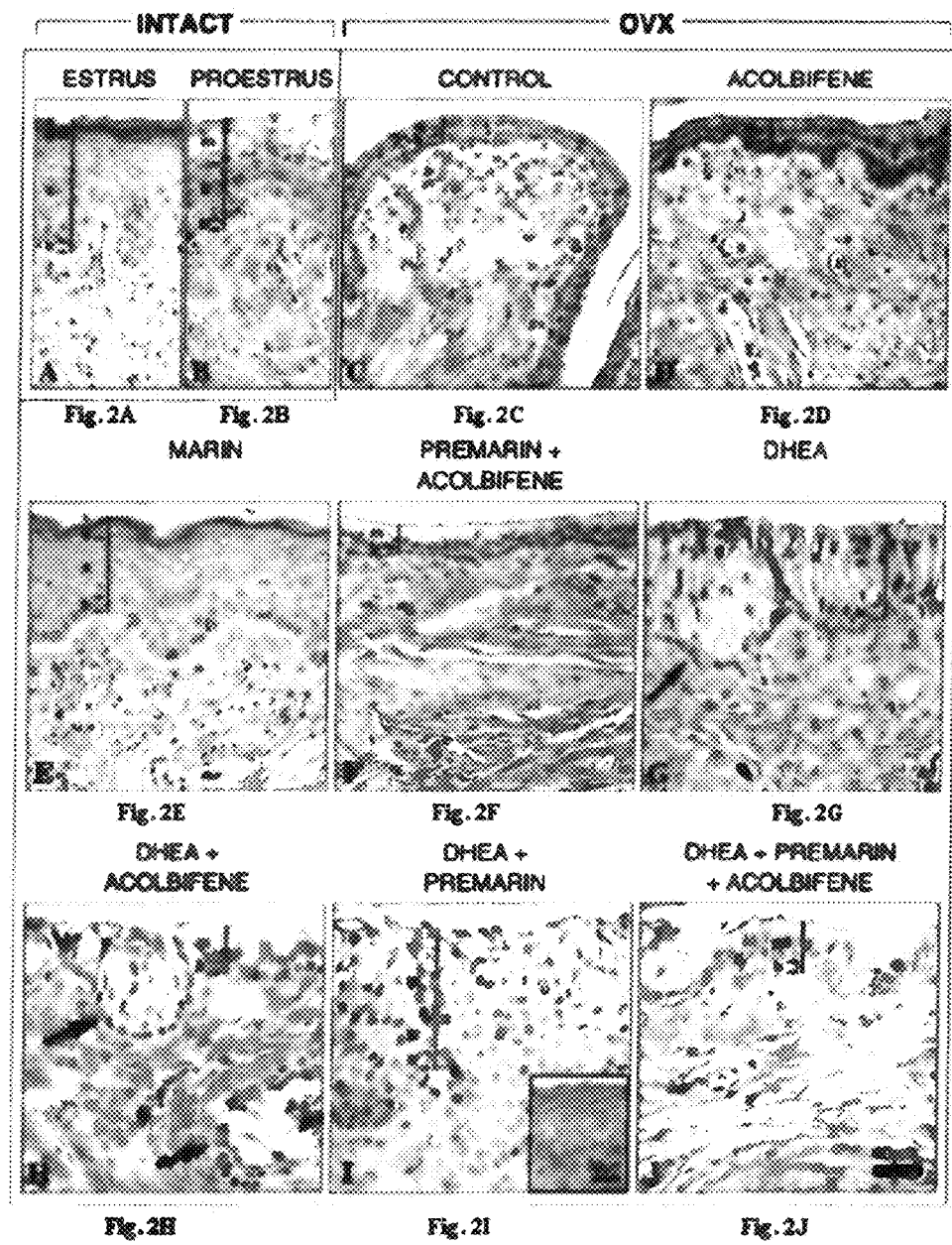

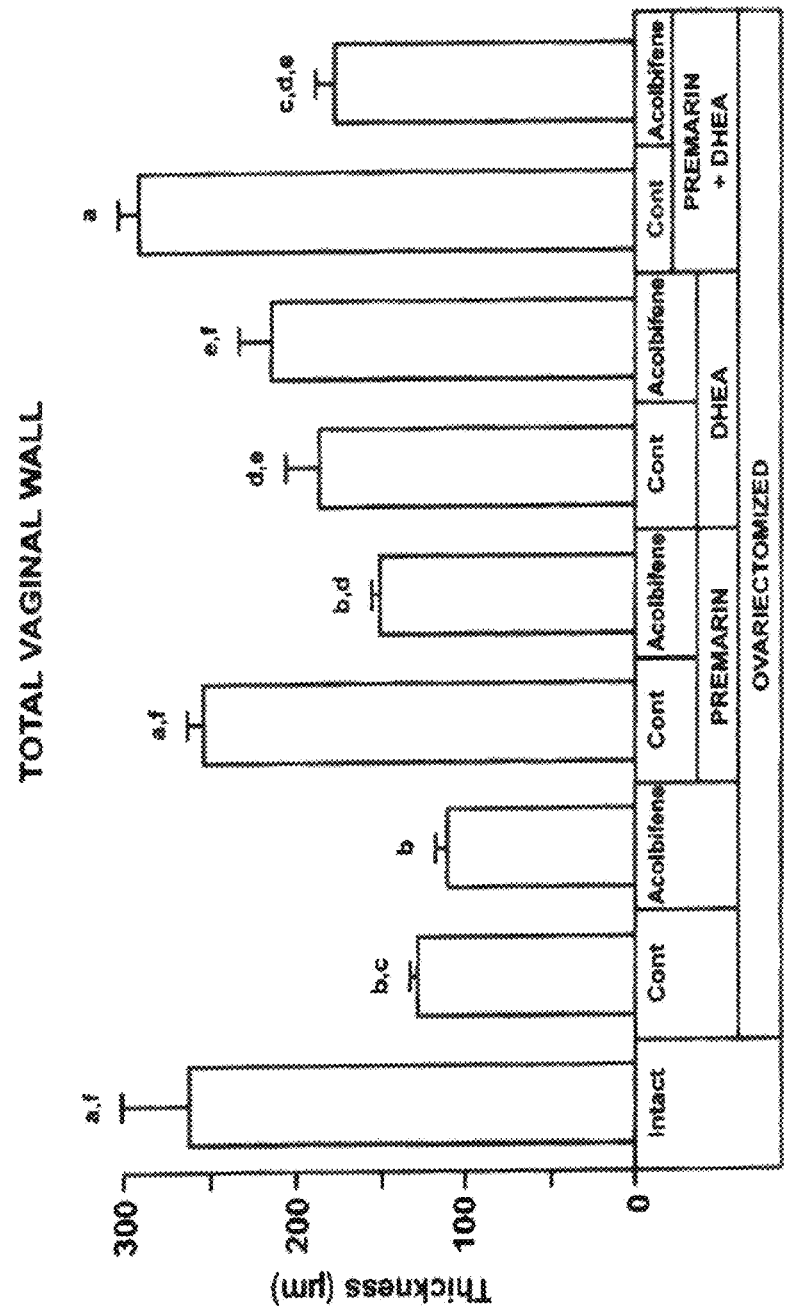

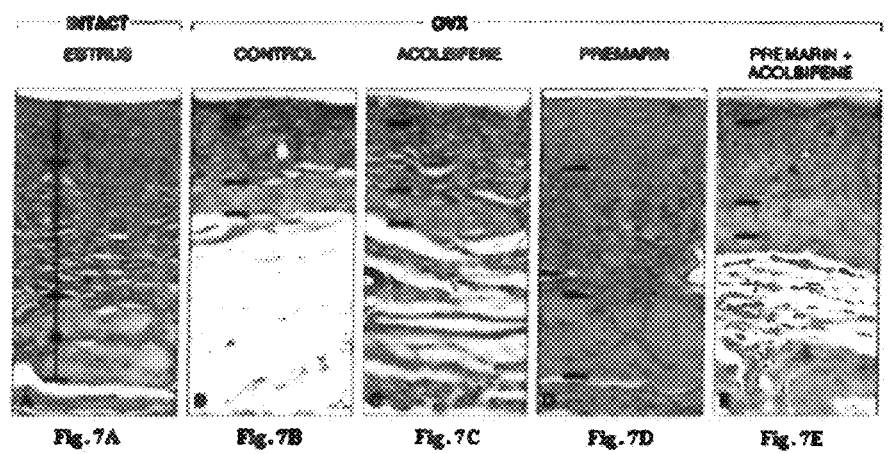
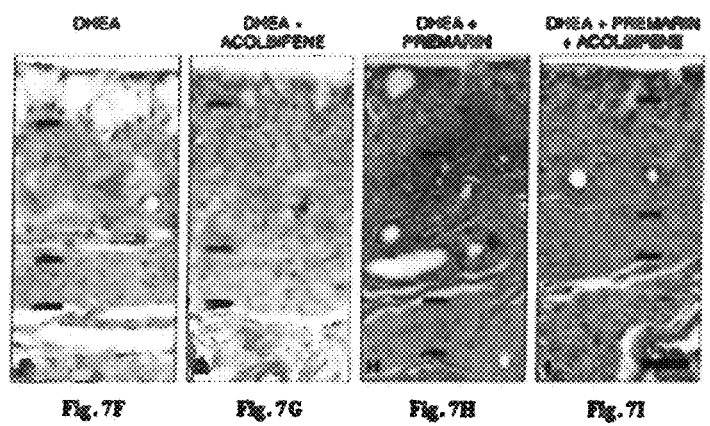

| | OVX | | | |
|---|---|---|---|---|
| CONT | ACOL | ERA-923 | TSE-424 | |
| R-54-01 | R-54-01 | R-54-01 | R-54-01 | |
| | 8 months | | | |
| | vagina cut in 7 cross-segments | | | |
| squamous stratified, 4-6 layers, non keratinizated | squamous stratified, 9-11 layers, keratinizated | squamous stratified, 9-11 layers, keratinizated | squamous stratified, 8-10 layers, keratinizated | |

Comparison between different SERMs: vaginal epithelial morphology, in the rat (X 200)

Fig. 10A  Fig. 10B  Fig. 10C  Fig. 10D

Comparison between different SERMs: vaginal epithelial morphology in the rat (X 200)

| | OVX | | | |
|---|---|---|---|---|
| CONT | ACOL | ERA-923 | TSE-424 | |
| R-54-01 | R-54-01 | R-54-01 | R-54-01 | |
| | | 8 months | | |
| | vagina cut in 7 cross-segments | | | |
| A basal cell layer overlaid by 1-2 layer(s) of small atrophic cuboidal cells (approx. 80% of the surface), or small cylindrical mucus cells (20%). Atrophic pattern strongly dominating. | A basal cell layer overlaid by one layer of cylindrical mucus cells (approx. 70-90% of the surface), or cuboidal atrophic (10-30%). Mucification pattern dominating. | A basal cell layer overlaid by one layer of tall cylindrical mucus cells (approx. 60-90% of the surface), or cuboidal atrophic (10-40%). Mucification pattern dominating. | A basal cell layer overlaid by 1-2 layer(s) of atrophic cuboidal cells by 1 layer of atrophic cells + 1 layer of small mucous cells. Atrophic pattern moderately dominating. | |

Fig. 10E     Fig. 10F     Fig. 10G     Fig. 10H

OVX - UNTOUCHED

SEG 4

SEG 6

PLACEBO

SEG 4

SEG 6

DHEA 0.33 mg / suppository

SEG 4

SEG 6

DHEA 0.66 mg / suppository

SEG 4

SEG 6

DHEA 1.00 mg / suppository

SEG 4

SEG 6 ized="1"># SEX STEROID PRECURSORS ALONE OR IN COMBINATION WITH SELECTIVE ESTROGEN RECEPTOR MODULATORS FOR THE PREVENTION AND TREATMENT OF SEXUAL DYSFUNCTION IN POSTMENOPAUSAL WOMEN

CROSS-REFERENCE TO RELATED APPLICATIONS

This is a divisional of U.S. patent application Ser. No. 14/464,536, filed Aug. 20, 2014 which is a divisional of U.S. patent application Ser. No. 11/255,617, filed Oct. 20, 2005, now U.S. Pat. No. 8,835,413, issued Sep. 16, 2014, entitled "SEX STEROID PRECURSORS ALONE OR IN COMBINATION WITH A SELECTIVE ESTROGEN RECEPTOR MODULATOR AND/OR WITH ESTROGENS AND/OR A TYPE 5 CGMP PHOSPHODIESTERASE INHIBITOR FOR THE PREVENTION AND TREATMENT OF DRYNESS AND SEXUAL DYSFUNCTION IN POSTMENOPAUSAL WOMEN", which application claims the benefit of the priority of U.S. Provisional Application No. 60/620,452 filed Oct. 20, 2004, the contents of which are specifically incorporated by reference herein. Applicants claim priority to each of the foregoing related applications.

FIELD OF THE INVENTION

The present invention relates to a method for treating or reducing the likelihood of acquiring problems affecting the layer lamina propria or the layer muscularis of the vagina using sex steroid precursors alone or in a novel combination therapy on susceptible warm-blooded animals, including humans. In particular, the combinations include administering a selective estrogen receptor modulator (SERM) and raising the patient's level of precursors of sex steroids, said precursor being selected from the group consisting of dehydroepiandrosterone (DHEA), dehydroepiandrosterone sulfate (DHEA-S), and androst-5-ene-3β,17β-diol (5-diol). Estrogens may also be administered to conteract the potential effects of some SERMs on hot flashes and other menopausal symptoms. Type 5 cGMP phosphodiesterase inhibitor may also be administered to improve sexual activity. The invention also relates to kits and pharmaceutical compositions for practicing the foregoing combination.

In U.S. Pat. No. 5,843,932, was reported the effect on vaginal atrophy of one, three or six months treatment with DHEA administered at a dose of 30 mg twice daily in a solution of 50% ethanol-50% propylene glycol on an area of 2 cm$^2$ of the dorsal skin in ovariectomized rat. Histopathologic examination showed proliferation and murification of the vaginal epithelium and reversal of vaginal mucosal atrophy in the rats treated with DHEA.

The study performed with the rat when DHEA was applied on the dorsal skin for 1, 3 and 6 months examined only the effect on the vaginal epithelium (Sourla et al., 1998, J. Steroid Biochem Mol Biol., 66(3): 137-149) and not on the two other layers, namely the lamina propria and the muscularis. It was then observed that DHEA was about 10 times more efficient on the vaginal epithelium when applied topically than when administered on the skin at a site distant from the vagina, thus requiring systemic absorption to exert its action.

In a previous study on the effect of DHEA administered on the skin in postmenopausal women for 12 months in a 10% DHEA cream, only the estrogenic activity of DHEA was evaluated (Labrie et al., 1997, J. Clin. Endocrinol. Metab., 82: 3498-3505). It was indicated (page 3500) "Vaginal cytology was examined as specific parameter of the estrogenic action of DHEA". This is due to the method of evaluation, namely vaginal smear which is limited to the superficial and easily removed cells of the epithelium.

The present invention describes the effects of DHEA and other components on the three layers of the vagina, namely the muscularis, the lamina propria and the epithelium with novel benefits at the three levels. The beneficial effects of DHEA on the lamina propria and muscularis are believed to be of major importance for the positive action of inhibitors of type 5 cGMP phospho-diesterase, such as viagra and other compounds or prostaglandin E1.

BACKGROUND OF THE RELATED ART

Vaginal dryness affects about 50% of postmenopausal women at the age of 50 to 60 years and 72% after 70 years (Rossin-Amar, 2000, Gynecol Obstet Fertil, 28(3): 245-249). Of these women, about 80% experience urogenital disorders, especially vaginitis and dyspareunia (Pandit and Ouslander, 1997, Am J Med Sci, 314(4): 228-31). Since these problems are believed to be at least partially related to a deprivation of sex steroids, appropriate local hormonal replacement therapy should be considered at menopause. It has recently been recognized that postmenopausal women are not only deprived of all ovarian estrogens but they are also progressively deprived of the androgens originating from the peripheral intracrine transformation of dehydroepiandrosterone (DHEA) into both androgens and estrogens (Labrie et al., 1991, Mol Cell Endocrinol, 78: C113-C118; Labrie et al., 1995, Ann NY Acad Sci, 774: 16-28; Labrie et al., 2003, End Rev, 24(2): 152-182). In fact, serum DHEA and DHEA-S progressively decrease from the age of 30 to 40 years (Labrie et al., 2003, End Rev, 24(2): 152-182; Orentreich et al., 1984, J Clin Endocrinol Metab, 59: 551-555; Labrie et al., 1997, J Clin Endocrinol Metab, 82: 2396-2402). A series of studies indicate that low levels of DHEA and DHEA-S are associated with a series of age-related morbidity and diseases (Labrie et al., 1997, J. Clin. Endocrinol. Metab., 82: 3498-3505; Helzlsouer et al., 1992, Cancer Res, 52(1): 1-4; Szathmari et al., 1994, Osteoporos Int, 4(2): 84-88; Thoman and Weigle, 1989, Adv Immununol, 46: 221-261; Barrett-Connor et al., 1999, J Reprod Med, 44(12): 1012-1020; Barrett-Connor et al., 1999, J Am Geriatr Soc, 47(6): 685-691).

An efficient approach to alleviate vaginal dryness and other menopausal symptoms is the use of hormone replacement therapy (HRT) (Greendale and Judd, 1993, J Am Geriatr Soc, 41(4): 426-436; Studd et al., 1980, Pasetto, Paleotti and Ambrus Eds, M T Press, Lancaster, p: 127-139). Recent clinical studies, however, have indicated that combining estrogens and progestins increases the incidence of breast cancer with a potential negative impact on cardiovascular events (Colditz et al., 1995, N Engl J Med, 332: 1589-1593; Ross et al., 2000, J Natl Cancer Inst, 92(4): 328-332; Rossouw et al., 2002, JAMA, 288(3): 321-333). Meanwhile, there is an increasing interest in the potential of combined estrogen-androgen replacement therapy (Rosenberg et al., 1997, J Reprod Med, 42(7): 394-404; Burd et al., 2001, Curr Women Health Rep, 1(3):202-205), although the use of the estrogenic component is limited by the potential complications mentioned above. Based upon recent advances in our understanding of human sex steroid physiology, especially in postmenopausal women (Labrie et al., 1991, Mol Cell Endocrinol, 78: C113-C118; Labrie et al., 2003, End Rev, 24(2): 152-182), the use of DHEA becomes a possibility to provide postmenopausal women with the appropriate levels of androgens and estrogens synthesised in specific tissues by intracrine mechanisms, with no systemic effects (Labrie et al., 1997, J. Clin. Endocrinol. Metab., 82: 3498-3505: 16-28; Labrie et al., 2003, End Rev, 24(2): 152-182; Labrie, 2001, Ref Gyn Obstet, 8: 317-322; Lasco et al., 2002, 145: 457-461). The restauration of androgen-sensitive elements of vaginal function should also help the action of inhibitors of type 5 cGMP phosphodiesterase or prostaglandin E1.

The selective estrogen receptor modulator (SERM) Acolbifene (EM-652) is a benzopyran derivative originally developed for the prevention and treatment of breast cancer (Gauthier et al., 1997, J Med Chem, 40: 2117-2122). Acolbifene is the compound having the highest affinity of all known compounds for the ER (Gauthier et al., 1997, J Med Chem, 40: 2117-2122; Labrie et al., 1999, J Steroid Biochem Mol Biol, 69 (1-6): 51-84; Tremblay et al., 1997, Mol. Endocrinol., 11: 353-365) and it exerts its activity on both ERα and ERβ (Tremblay et al., 1998, Endocrinology, 139: 111-118). This compound displays a pure and highly potent antiestrogenic activity in the mammary gland and endometrium while decreasing serum cholesterol and triglycerides and preventing bone loss, at least in the rat (Labrie et al., 1999, J Steroid Biochem Mol Biol, 69 (1-6): 51-84). Moreover, it has been demonstrated that the administration of DHEA, not only does not interfere, but does exert an additive inhibitory effect with the pure antiestrogen Acolbifene on human breast tumour growth in the nude mouse (Dauvois et al., 1991, Cancer Res, 51: 3131-3135; Luo et al., 1997, Endocrinology, 138: 4435-4444). Combined treatment of DHEA and Acolbifene has been proposed as a beneficial chemopreventive and therapeutic approach in breast cancer (Labrie, 2001, Ref Gynecol Obstet, 8: 317-322). In fact, the inhibitory effect of DHEA on the growth of human breast cancer xenografts in nude mice supports its use as hormone replacement therapy (Dauvois et al., 1991, Cancer Res, 51: 3131-3135; Couillard et al., 1998, J Natl Cancer Inst, 90: 772-778).

WO 99/63974 disclosed medical uses of a selective estrogen receptor modulator in combination with sex steroid precursors

SUMMARY OF THE INVENTION

It is accordingly an object of the present invention to provide effective methods of treatment for vaginal problems, more particularly vaginal dryness, dyspareunia, and sexual dysfunction which can lead to decrease in sexual desire and activity while minimizing undesirable side effects.

It is another object to provide methods of reducing the risk of acquiring the above problems.

In one embodiment, the invention pertains to a method of treating or reducing the risk of acquiring vaginal dryness comprising increasing levels of a sex steroid precursor selected from the group consisting of dehydroepiandrosterone (DHEA), dehydroepiandrosterone-sulfate (DHEA-S) and androst-5-ene-3β,17β-diol (5-diol), in a subject or patient in need of said treatment or said steroid precursor, and further comprising administering to said patient a therapeutically effective amount of a selective estrogen receptor modulator (SERM) as part of a combination therapy.

In another embodiment, the invention includes additional administration of estrogens to conteract the effects of SERMs on hot flashes and other menopausal symptoms.

In another embodiment, the invention includes additional administration of a Type 5 cGMP phosphodiesterase inhibitor or prostaglandin E1 to improve sexual activity.

As used herein, a selective estrogen receptor modulator (SERM) is a compound that either directly or through its active metabolite functions as an estrogen receptor antagonist ("antiestrogen") in breast tissue, yet provides estrogenic or estrogen-like effect on bone tissue and on serum cholesterol levels (i.e. by reducing serum cholesterol). Non-steroidal compounds that function as estrogen receptor antagonists in vitro or in human or rat breast tissue (especially if the compound acts as an antiestrogen on human breast cancer cells) is likely to function as a SERM. Conversely, steroidal antiestrogens tend not to function as SERMs because they tend not to display any beneficial effect on serum cholesterol. Non-steroidal antiestrogens we have tested and found to function as SERMs include EM-800, EM-01538, Raloxifene, Tamoxifen, Droloxifene, Toremifene, Idoxifene, TSE-424, ERA-923, Lasoxifene (CP 336156), Arzoxifene (LY 353 381) and GW-5638. We have tested the steroidal antiestrogen ICI 182,780 and found not to function as SERM. SERMs, in accordance with the invention may be administered in the same dosage as known in the art when these compounds are used as antiestrogens.

Without intending to be bound by theory, it is believed that SERMs, many of which, preferably, have two aromatic rings linked by one to two carbon atoms, are expected to interact with the estrogen receptor by virtue of the foregoing portion of the molecule that is best recognized by the receptor. Preferred SERMs have side chains which may selectively cause antagonistic properties in breast tissue without having significant antagonistic properties in other tissues. Thus, the SERMs may desirably functions as antiestrogens in the breast while surprisingly and desirably functioning as estrogens (or providing estrogen-like activity) in bone and on the blood components (where concentrations of lipids and/or cholesterol are favorably affected). The favorable effect on cholesterol and/or lipids potentially translates to a favorable effect against atherosclerosis which is known to be adversely affected by improper levels of cholesterol and lipids.

In another embodiment, the invention includes method, pharmaceutical composition and kit wherein the selective estrogen receptor modulator has a molecular formula with the following features:

a) two aromatic rings spaced by 1 to 2 intervening carbon atoms, both aromatic rings being either unsubstituted or substituted by a hydroxyl group or a group converted in vivo to hydroxyl;

b) a side chain possessing an aromatic ring and a tertiary amine function or salt thereof.

It is preferred that the side chain is selected from the group consisting of:

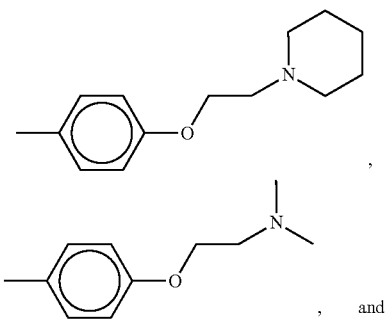

, and

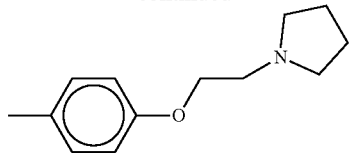

It is also preferred that the two aromatic rings are both phenyl and that the side chain possesses a moiety selected from the group consisting of a methine, a methylene, —CO—, —O—, and —S—, an aromatic ring, and a tertiary amine function or salt thereof.

In another embodiment, the selective estrogen receptor modulator is selected from the group consisting of a benzothiophene derivative, triphenylethylene derivative, indole derivative, benzopyran derivative, 5,6,7,8-tetrahydronaphtalene and centchroman derivative.

In one embodiment, it is preferred that the selective estrogen receptor modulator is a benzothiophene derivative compound of the following formula:

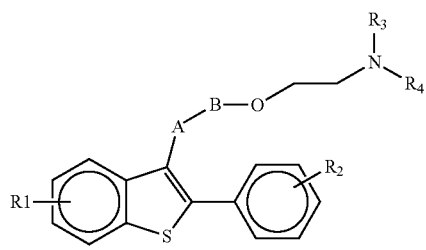

wherein $R_1$ and $R_2$ are independently selected from the group consisting of: hydrogen, hydroxyl, and a moiety converted in vivo in hydroxyl;

wherein $R_3$ and $R_4$ are either independently selected from the group consisting of: C1-C4 alkyl, or wherein $R_3$, $R_4$ and the nitrogen to which they are bound, together are any structure selected from the group consisting of pyrrolidino, dimethyl-1-pyrrolidino, methyl-1-pyrrolidinyl, piperidino, hexamethyleneimino and morpholino;

wherein A is selected from the group consisting of —CO—, —CHOH, and —CH$_2$—;

wherein B is selected from the group consisting of phenylene, pyridylidene, and -cycloC$_4$H$_2$N$_2$—.

Particularly, the selective estrogen receptor modulator is selected from the group consisting of Raloxifene, Arzoxifene (LY 353381) and LY 335563.

In another embodiment, it is preferred that the selective estrogen receptor modulator is a triphenylethylene derivative compound of the following formula:

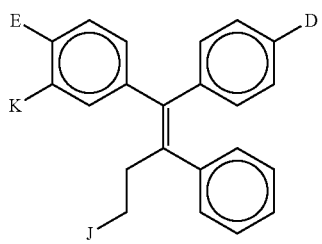

wherein D is —OCH$_2$CH$_2$N(R$_3$)R$_4$ or —CH=CH—COOH (R$_3$ and R$_4$ either being independently selected from the group consisting of C1-C4 alkyl, or R$_3$, R$_4$, and the nitrogen atom to which they are bound, together being a ring structure selected from the group consisting of pyrrolidino, dimethyl-1-pyrrolidino, methyl-1-pyrrolidinyl, piperidino, hexamethyleneimino and morpholino);

wherein E and K are independently hydrogen or hydroxyl;
wherein J is hydrogen or halogen.

Particularly, selective estrogen receptor modulator is Tamoxifen, OH-tamoxifen, Droloxifene, Toremifene, Iodoxifene, and GW 5638.

In another embodiment, it is preferred that the selective estrogen receptor modulator is an indole derivative compound of the following formula:

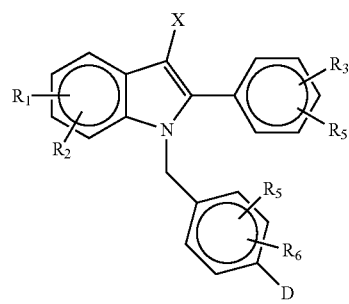

wherein D is selected from the groups consisting of —OCH$_2$CH$_2$N(R$_7$)R$_8$, —CH=CH—CO N(R$_7$)R$_8$, —CC—(CH$_2$)$_n$—N(R$_7$)R$_8$ (R$_7$ and R$_8$ either being independently selected from the group consisting of C$_1$-C$_6$ alkyl, or R$_7$, R$_8$ and the nitrogen atom to which they are bound, together being a ring structure selected from the group consisting of pyrrolidino, dimethyl-1-pyrrolidino, methyl-1-pyrrolidinyl, piperidino, hexamethyleneimino, morpholino, ring);

wherein X is selected from the group consisting of: hydrogen, and C1-C6 alkyl;

wherein $R_1$, $R_2$ $R_3$, $R_4$, $R_5$, and $R_6$ are independently selected from the group consisting of: hydrogen, hydroxyl, C$_1$-C$_6$ alkyl, and a moiety converted in vivo in hydroxyl. Particularly, the selective estrogen receptor modulator is TSE-424 and ERA-923.

In another embodiment, it is preferred that the selective estrogen receptor modulator is a compound of the following formula:

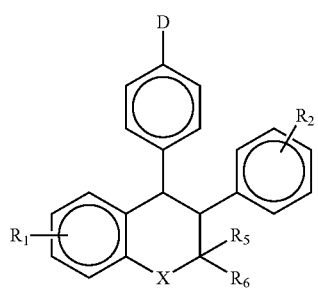

wherein $R_1$ and $R_2$ are independently selected from the group consisting of: hydrogen, hydroxyl, and a moiety converted in vivo in hydroxyl;

wherein $R_5$ and $R_6$ are independently hydrogen or C$_1$-C$_6$ alkyl;

wherein D is —OCH$_2$CH$_2$N(R$_3$)R$_4$ (R$_3$ and R$_4$ either being independently selected from the group consisting of $C_1$-$C_4$ alkyl, or $R_3$, $R_4$ and the nitrogen atom to which they are bound, together being a ring structure selected from the group consisting of pyrrolidino, dimethyl-1-pyrrolidino, methyl-1-pyrrolidinyl, piperidino, hexamethyleneimino, morpholino).

Wherein X is selected from the group consisting of —O— and —$CH_2$—. Particularly, the compound is selected from the group consisting of: (−)-cis-(5R,6S)-6-phenyl-5-[4-(2-pyrrolidin-1-ylethoxy)phenyl]-5,6,7,8-tetrahydronaphthalen-2-ol, D-(−)-tartrate salt (lasofoxifene) and (3,4-trans-2,2-dimethyl-3-phenyl-4-[4-(2-(2-(pyrrolidin-1-yl)ethoxy)phenyl]-7-methoxychroman).

In another embodiment, it is preferred that the selective estrogen receptor modulator has the following formula:

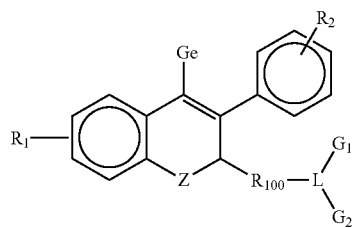

wherein $R_1$ and $R_2$ are independently hydrogen, hydroxyl or a moiety which is converted to hydroxyl in vivo;
wherein Z is a bivalent closing moiety, particularly, Z is selected from the group consisting of —O—, —NH—, —S—, and —$CH_2$—;
wherein the R100 is a bivalent moiety which distances L from the B-ring by 4-10 intervening atoms;
wherein L is a bivalent or trivalent polar moiety selected from the group of —SO—, —CON—, —N<, and —SON<;
wherein $G_1$ is selected from the group consisting of hydrogen, a $C_1$ to $C_5$ hydrocarbon or a bivalent moiety which joins $G_2$ and L to form a 5- to 7-membered heterocyclic ring, and halo or unsaturated derivatives of the foregoing.
wherein $G_2$ is either absent or selected from the group consisting of hydrogen, a $C_1$ to $C_5$ hydrocarbon or a bivalent moiety which joins $G_1$ and L to form a 5- to 7-membered heterocyclic ring, and halo or unsaturated derivatives of the foregoing;
wherein $G_3$ is selected from the group consisting of hydrogen, methyl and ethyl. More particularly, benzopyran derivatives of the following general structure are preferred:

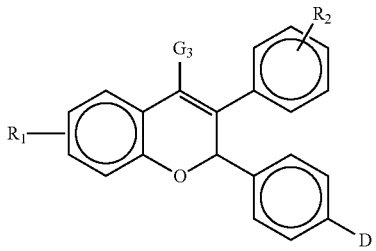

wherein D is —$OCH_2CH_2N(R_3)R_4$ ($R_3$ and $R_4$ either being independently selected from the group consisting of $C_1$-$C_4$ alkyl, or $R_3$, $R_4$ and the nitrogen atom to which they are bound, together being a ring structure selected from the group consisting of pyrrolidino, dimethyl-1-pyrrolidino, methyl-1-pyrrolidinyl, piperidino, hexamethyleneimino, morpholino, ring).

wherein $R_1$ and $R_2$ are independently selected from the group consisting of: hydrogen, hydroxyl, and a moiety converted in vivo in hydroxyl.

It is also preferred that benzopyran derivatives are optically active compounds having an absolute configuration S on carbon 2 or pharmaceutically acceptable salts thereof, said compounds having the molecular structure:

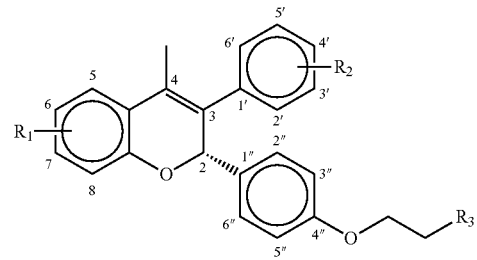

wherein $R_1$ and $R_2$ are independently selected from the group consisting of hydroxyl and a moiety convertible in vivo to hydroxyl;
wherein $R^3$ is a species selected from the group consisting of saturated, unsaturated or substituted pyrrolidinyl, saturated, unsaturated or substituted piperidino, saturated, unsaturated or substituted piperidinyl, saturated, unsaturated or substituted morpholino, nitrogen-containing cyclic moiety, nitrogen-containing polycyclic moiety, and NRaRb (Ra and Rb being independently hydrogen, straight or branched $C_1$-$C_6$ alkyl, straight or branched $C_2$-$C_6$ alkenyl, and straight or branched $C_2$-$C_6$ alkynyl).

In one embodiment, the benzopyran derivative is a salt of an acid selected from the group consisting of acetic acid, adipic acid, benzenesulfonic acid, benzoic acid, camphorsulfonic acid, citric acid, fumaric acid, hydroiodic acid, hydrobromic acid, hydrochloric acid, hydrochlorothiazide acid, hydroxy-naphthoic acid, lactic acid, maleic acid, methanesulfonic acid, methylsulfuric acid, 1,5-naphthalenedisulfonic acid, nitric acid, palmitic acid, pivalic acid, phosphoric acid, propionic acid, succinic acid, sulfuric acid, tartaric acid, terephthalic acid, p-toluenesulfonic acid, and valeric acid.

The preferred selective estrogen receptor modulators are:

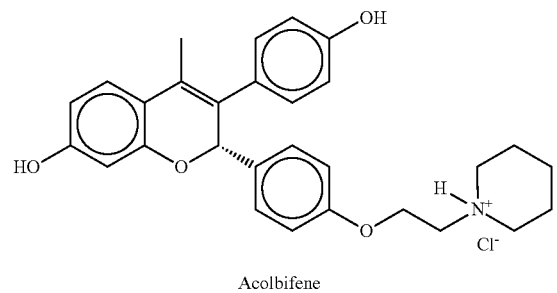

Acolbifene

Raloxifene, Arzoxifene, Tamoxifen, Droloxifene, Toremifene, Iodoxifene, GW 5638, TSE-424, ERA-923, and lasofoxifene.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 2A-2J show the vaginal epithelium histomorphology of segment 5 in the nine groups of rats. Bar in (J), 40 µm.

FIG. 2A is representative of the estrogenic effect, the stratified squamous epithelium of cycling rats at estrous consists of four main layers: one cell layer of stratum basale (b), 6 to 7 cell layers of stratum spinosum (s) and a stratum granulosum of 5 to 6 layers (g) overlaid by the stratum corneum (c) made of tightly packed flattened cornified cells.

FIG. 2B illustrates cycling rats at proestrus which are under an estrogenic-progestational influence, and is used to illustrate mucification. In most segments 2 to 7, one basal cell layer (b) was overlaid by 5 to 6 cell layers of stratum spinosum (s), and a stratum mucification (m) consisting of 3-4 layers of mucous cells.

FIG. 2C illustrates that in the OVX control, a basal cell layer (b) was overlaid by a layer of atrophic cuboidal cells (a).

FIG. 2D illustrates the vaginal epithelium of OVX rats treated with an daily oral dose of Acolbifene, (2.5 mg/kg) and shows atrophy, but with an outer layer of low columnar mucous cells (m) overlying the basal cell layer (b).

FIG. 2E illustrates vaginal epithelium of OVX rats treated with an daily oral dose of Premarin (0.5 mg/kg). The OVX-induced atrophy was replaced by an estrogenic pattern comparable to that found at estrus.

FIG. 2F illustrates that in OVX animals which received Premarin+Acolbifene, atrophy predominated with a morphology similar to that of Acolbifene-treated animals, although larger mucous cells were seen.

FIG. 2G illustrates that following treatment of OVX animals with a once daily cutaneous application of DHEA (80 mg/kg) on an area of 2×2 cm of the dorsal skin, an hypertrophic epithelium made of 3-5 layers of mucous cells (m) was seen overlying a basal layer (b). Several invaginations characterized this epithelium (arrow).

FIG. 2H illustrates that in most areas of the vaginal epithelium of DHEA+Acolbifene-treated animals, a layer of mucous cells (m) rested on a basal cell layer (b), while in some areas, many layers of mucous cells overlaid the basal cell layer. Several invaginations characterized this epithelium (arrows).

FIG. 2I illustrates that treatment with DHEA+Premarin led to a mixed epithelium composed of a three to seven cell layer-thick stratified squamous epithelium (s) overlaid by 3-5 layers of mucous cells (m) in 3 animals. In 2 animals, areas of stratified squamous epithelium were predominant (insert). Bar in insert, 30 µm.

FIG. 2J illustrates that when DHEA, Premarin and Acolbifene were combined, the epithelium was similar to that of the DHEA+Acolbifene group.

FIG. 3A shows severe inflammatory changes characterized by focal leukocyte infiltration with intraepithelial microabscess (M). FIG. 3B shows focal erosion (E) characterized by reduced epithelial thickness and ulceration (U) visualized as a complete disappearance of the epithelium.

FIGS. 5A-5D show the thickness (µm) of the three different vaginal compartments at the level of the fifth segment of the rat vagina: FIG. 5A epithelium, FIG. 5B lamina propria, FIG. 5C muscularis and FIG. 5D total thickness, after 36 weeks treatment of OVX animals with DHEA, Premarin and Acolbifene, alone or in combination. Intact animals at estrus and proestrus are added as reference controls. Groups sharing the same letter are not statistically different at $p<0.05$.

FIGS. 7A-7I show microphotographs of the three vaginal compartments: (E) epithelium, (L) lamina propria and (M) muscularis, at the level of the fifth segment of the rat vagina with emphasis on the relative muscularis thickness in the different groups. Separation of the 3 vaginal wall layers with bars is indicated to best estimate the thickness distribution between the different groups. FIG. 7A Intact, 7B OVX. Also illustrated is OVX treated with FIG. 7C Acolbifene, FIG. 7D Premarin, FIG. 7E Premarin+Acolbifene, FIG. 7F DHEA, FIG. 7G DHEA+Acolbifene, FIG. 7H DHEA+Premarin, FIG. 7I DHEA+Premarin+Acolbifene.

FIGS. 10A-10H show a comparison of indicated rat vaginal epithelial morphology following treatment with different SERMs (FIGS. 10B-10D and FIGS. 10F-10H) versus control (FIGS. 10A and 10E).

Figures 13A, 13B, 13C, 13D:
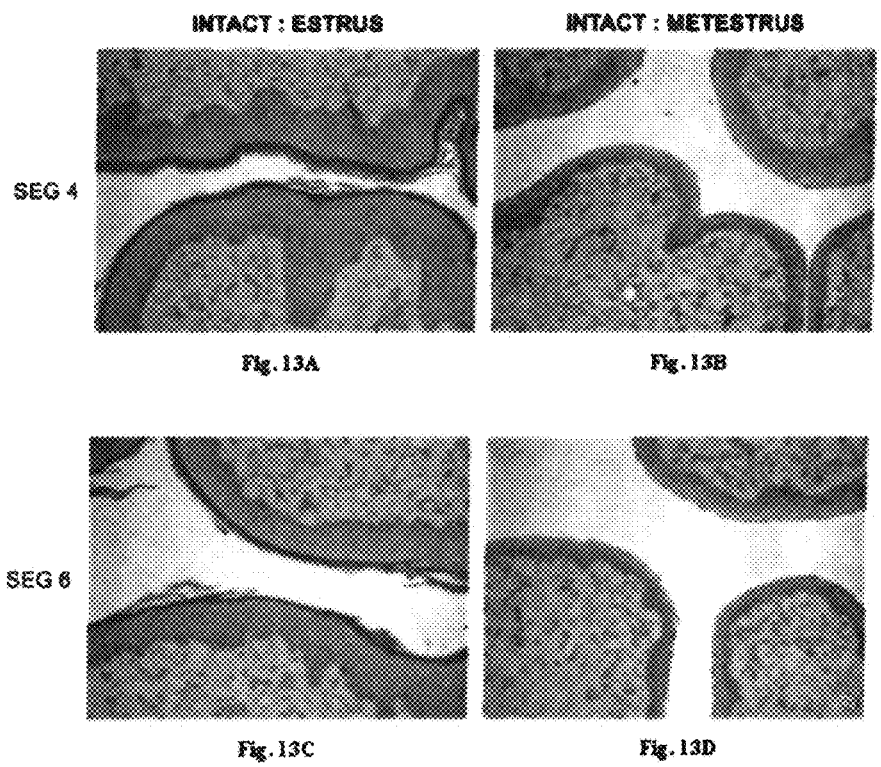
FIG. 13A-13D show the effect intact rat.

At estrus, the vaginal epithelium is 12-18 layer-thick in segment 4 (FIG. 13A) and 12-15 layer-thick in segment 6 (FIG. 13C).

At metestrus, the vaginal epithelium displays 6 to 10 cell layers in segment 4 (FIG. 13B), and 5 to 7 layers in segment 6 (FIG. 13D).

Figure 14A:
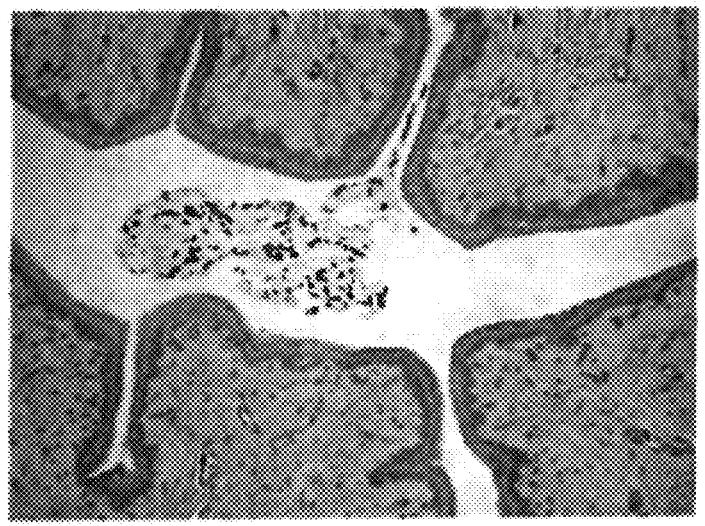
Figure 14B:
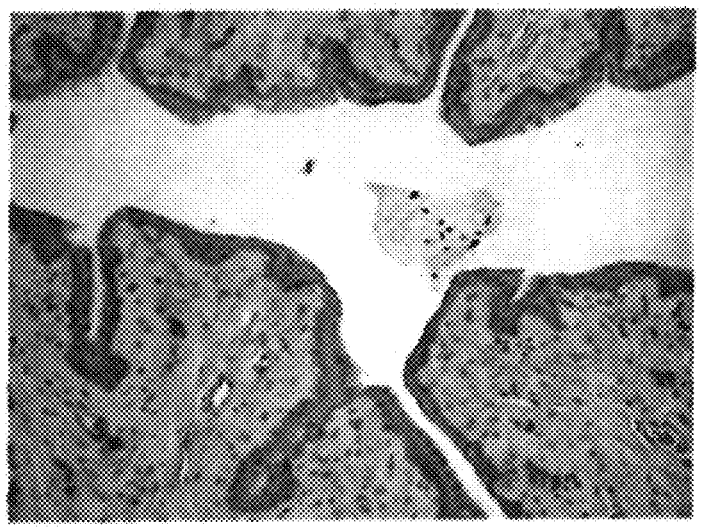

FIGS. 14A-14B show the effect OVARIECTOMIZED UNTOUCHED Rats. In segment 4, FIG. 14A, the vagina is lined by a squamous stratified epithelium of 2 to 6 cell layers. In segment 6, FIG. 14B, complete atrophy is observed, with flat 2 to 3 cell layers. Some rare foci of small cylindrical mucous cells could be seen throughout the whole vagina.

Figure 15A:
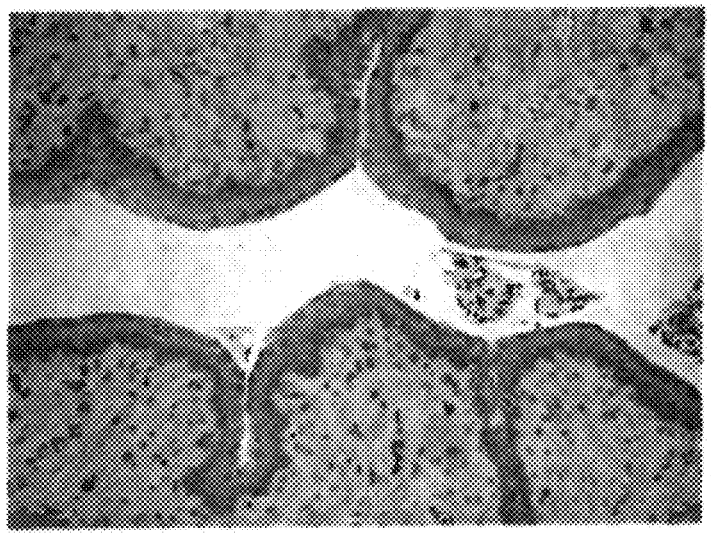
Figure 15B:
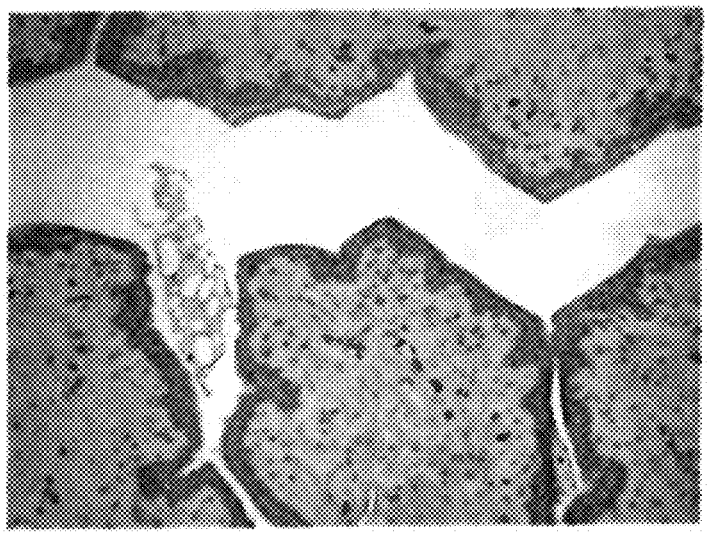

FIGS. 15A-15B show the effect of placebo/suppository. In comparison with the OVX untouched group, the vaginal squamous stratified epithelium of the placebo group was slightly thicker, with segment 4, FIG. 15A, displaying 4 to 8 cell layers. In segment 6, FIG. 15B, the same morphology as that of OVX untouched group was observed, with 2-3 epithelial cell layers. Foci of small cylindrical mucous cells could be found throughout the vagina, slightly more when compared with the OVX untouched animals.

Figure 16A:
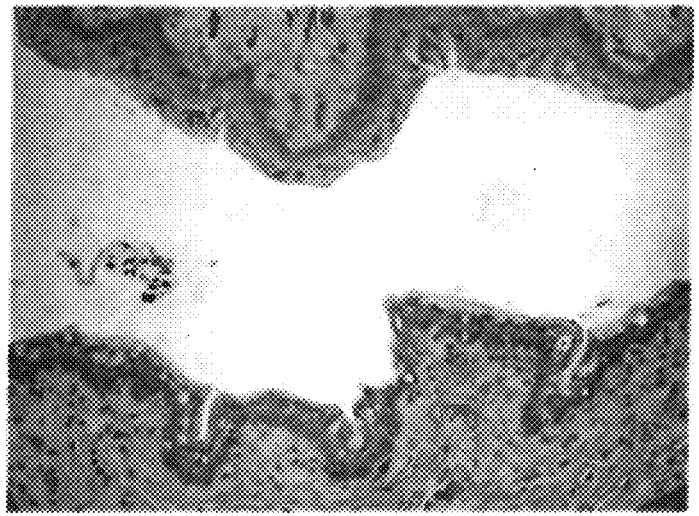
Figure 16B:
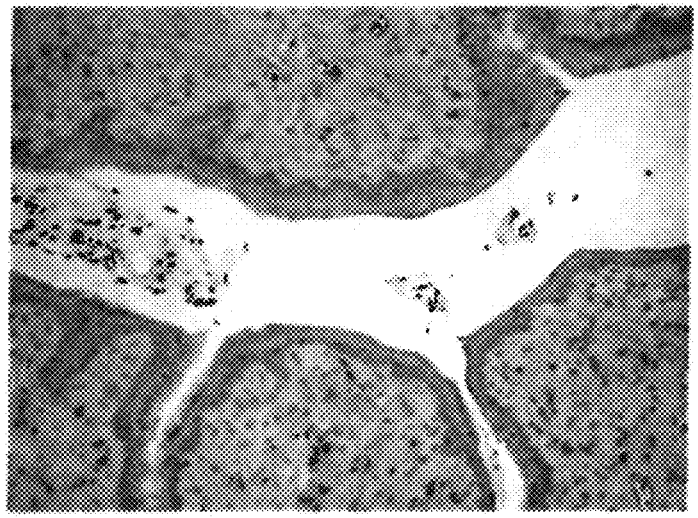

FIGS. 16A-16B show the effect of DHEA 0.33 mg/suppository. In segment 4, FIG. 16A, the vaginal epithelium is stratified squamous with 3 to 7 cell layers. About 20 to 60% of the vaginal lining consists of well-aligned mucous cells in alternance with 15 to 50% of hypertrophied mucous cells, overlying one or more squamous stratified epithelium layers, and with non-mucified areas. In segment 6, FIG. 16B, the epithelial thickness is reduced to almost the thickness found in OVX untouched animals: 2-5 cell layers overlaid by cylindrical mucous cells. A large variation in the occurrence of mucous cells was observed, these cells covering from 5 to 75% of the vaginal surface, in alternance with non-mucified areas.

Figure 17A:
Figure 17B:
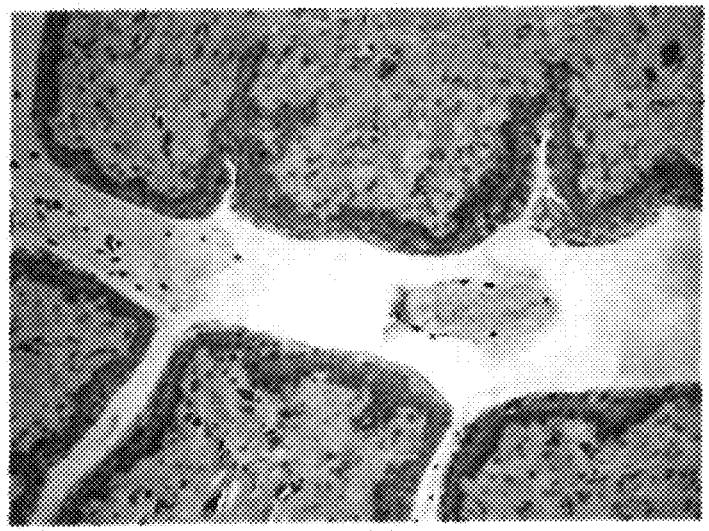

FIGS. 17A-17B show the effect of DHEA 0.66 mg/suppository. In segment 4, FIG. 17A, the stratified squamous epithelium is 3 to 6 cell layer-thick. About 5 to 20% of the vaginal lining consists of well-aligned mucous cells in alternance with 10 to 75% of hypertrophied mucous cells, overlying one or more squamous stratified epithelium layers. Non-mucified epithelial areas are also present. In segment 6, FIG. 17B, the epithelial thickness is reduced and consists of a squamous stratified epithelium of 2 to 4 cell layers, surmounted by a layer of well-aligned mucous cells. Mucified areas varied from 20 to 80% of the vaginal surface, in alternance with non-mucified areas.

Figure 18A:
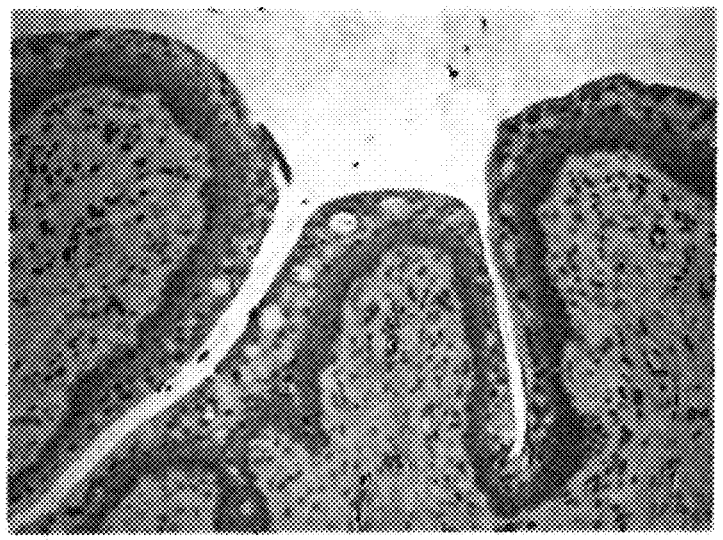
Figure 18B:
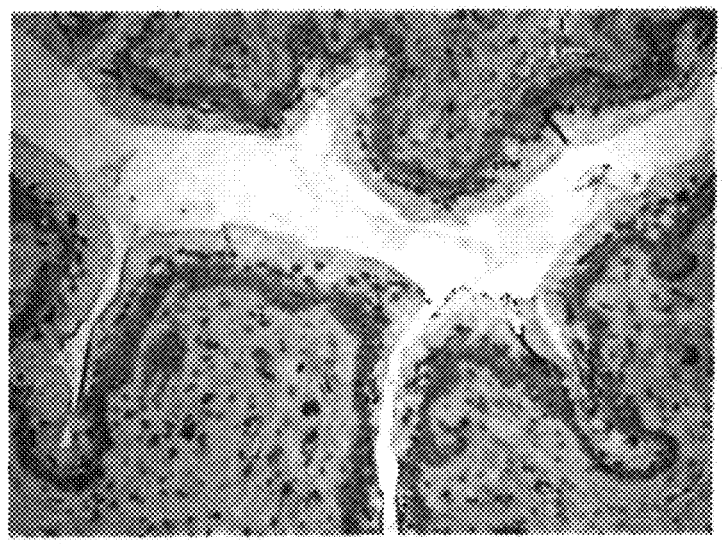

FIGS. 18A-18B show the effect of DHEA 1 mg/suppository. In segment 4, FIG. 18A, the stratified squamous epithelium displays 3 to 9 cell layers. Hypertrophied mucous cells overlying 3 to 4 squamous cell layers cover 50 to 70% of the vaginal surface, while well-aligned mucous cells line 5 to 30% of the vaginal surface. Non-mucified areas are interspersed between mucified cells. In segment 6, FIG. 18B, the epithelial thickness is also reduced and consists of 2 to 4 cell layers. Hypertrophied mucous cells overlying 1 to 3 squamous cell layers cover about 30 to 100% of the vaginal surface while well-aligned mucous cells cover 0 to 70%. Few interspersed non-mucified areas are also observed.

Figure 19:
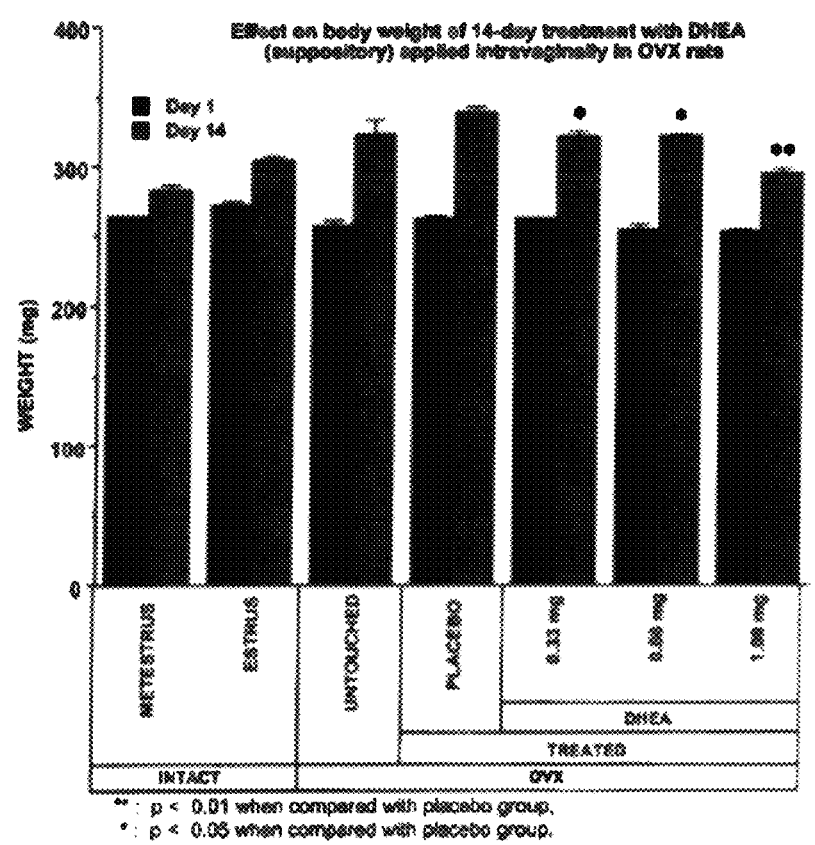

FIG. 19 is a graph of the effect on body weight of 14-day treatment with DHEA (suppository) applied intravaginally in OVX rats. Compared with placebo group, the body weight of the groups given DHEA at doses of 0.33 mg and 0.66 mg slightly decreased, while the decrease was more pronounced in the 1 mg group.

Figure 20:
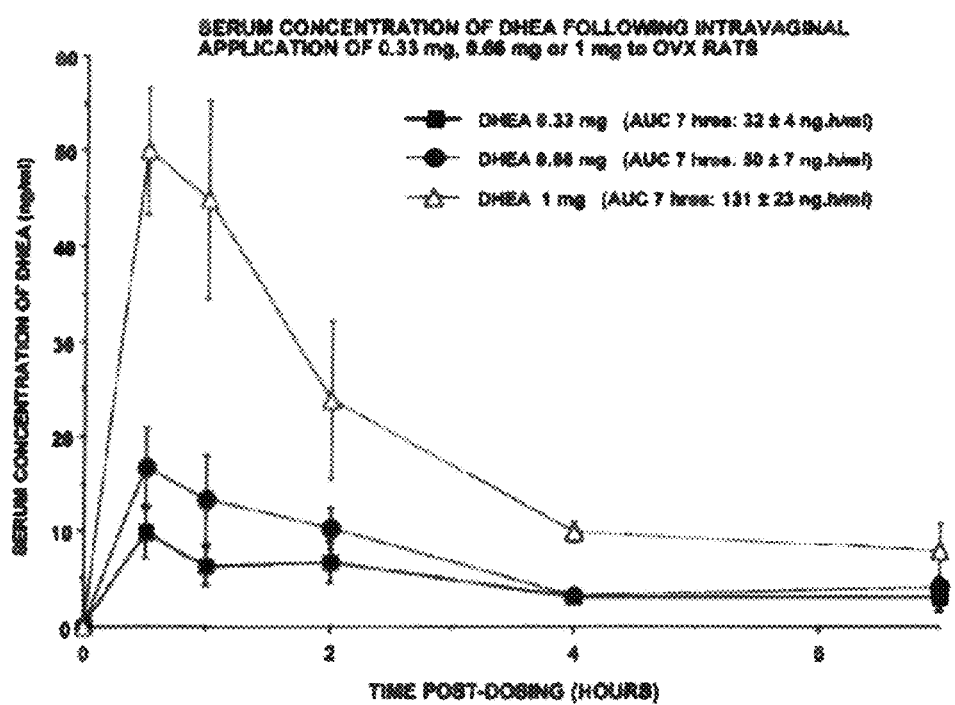

FIG. 20 is a graph of the serum concentration of DHEA following intravaginal application of 0.33 mg, 0.66 mg or 1 mg to OVX rats. Area under the curve (AUC) values seven hours following DHEA treatment were 32±4 ng·h/ml, 50±7 ng·h/ml and 131±23 ng·h/ml when DHEA was given at the doses of 0.33 mg, 0.66 mg or 1 mg, respectively.

DETAILED DESCRIPTION OF THE INVENTION

After cessation of estrogen secretion by the ovaries at menopause, practically all androgens and estrogens are synthesized in peripheral target tissues by intracrine mechanisms from dehydroepiandrosterone (DHEA) of adrenal origin. In fact, in the absence of ovarian estrogens, the gradual decrease in serum DHEA is likely to play an important role in the vaginal dryness, inflammation, dyspareunia and sexual dysfunction frequently associated with menopause. In order to assess the specific estrogenic and/or androgenic effects of a potential novel hormone replacement therapy that could, among other beneficial effects, alleviate vaginal dryness, we have examined the morphology of the rat vagina eight months after ovariectomy (OVX) and treatment of OVX animals with DHEA, conjugated estrogens (Premarin) and the selective estrogen receptor modulator Acolbifene, administered alone or in combination. In intact animals at estrus and in OVX rats treated with Premarin, the typical vaginal estrogenic pattern is a keratinized stratified squamous epithelium. OVX led to a general atrophy associated with inflammatory changes while Acolbifene reduced the inflammation incidence and increased the number and size of mucous cells in the vaginal epithelium. At the doses used, Premarin completely reversed the OVX-induced epithelial atrophy, while DHEA partially reversed the atrophy. In fact, the vaginal epithelium of OVX animals treated with DHEA became hyperplastic with 3-5 layers of columnar mucous and goblet cells typical of an androgenic effect. The addition of Premarin to DHEA led to an epithelium thicker than in intact animals. Moreover, compactness of the collagen fibers in the lamina propria was increased by DHEA. On the other hand, treatment with Acolbifene alone showed a tendency for an increase in the lamina propria thickness, which reached intact values when combined with DHEA.

After OVX, the vaginal muscular layer was decreased by 46%, an effect which was 41% and 100% reversed by DHEA and Premarin, respectively. On the other hand, the 50% decrease in total vaginal wall thickness following OVX was 42% and 93% reversed by DHEA and Premarin, respectively, while the combination of DHEA and Acolbifene reversed total vaginal wall thickness to a value not significantly different from intact control animals.

Immunohistochemistry revealed strong androgen receptor (AR) labeling in all DHEA-treated groups. On the other hand, estrogen receptor alpha (ERα) and progesterone receptor (PR) labeling were not detected in any of the Acolbifene-treated groups.

In conclusion, treatment with DHEA or the combination of DHEA and Acolbifene partially or completely prevents the OVX-induced atrophic changes observed in various layers of the vaginal wall through a predominant androgenic effect, as revealed by epithelial mucification and AR up-regulation. The present data also show particularly interesting effects of DHEA on the three layers of the vaginal wall, namely a highly mucified epithelium, an increased compactness of the collagen fibers in the lamina propria as well as an increase of the muscularis thickness. DHEA thus exerts both androgenic and estrogenic effects on the vaginal mucosa, thus providing a more physiological replacement therapy. While each of the examined compounds has potential beneficial effects on vaginal function, DHEA alone or in combination could well optimally relieve vaginal dryness and restore global vaginal physiology and help correcting sexual dysfunction associated with menopause. DHEA and other components could be administered locally or systemically.

A selective estrogen receptor modulator of the invention has a molecular formula with the following features: a) two aromatic rings spaced by 1 to 2 intervening carbon atoms, both aromatic rings being either unsubstituted or substituted by a hydroxyl group or a group converted in vivo to hydroxyl; and b) a side chain possessing an aromatic ring and a tertiary amine function or salt thereof.

One preferred SERM of the invention is EM-800 reported in PCT/CA96/00097 (WO 96/26201) The molecular structure of EM-800 is:

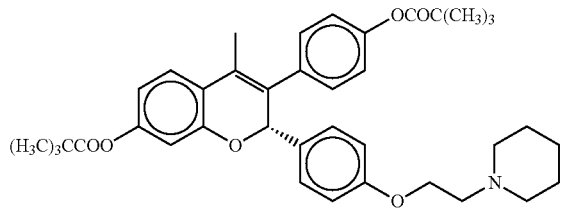

Another preferred SERM of the invention is acolbifene (EM-1538, also called EM-652.HCl) reported in U.S. Pat. No. 6,710,059 B1

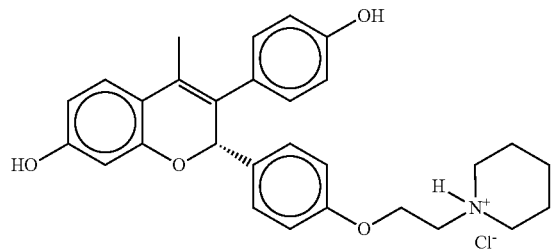

is the hydrochloride salt of the potent antiestrogen EM-652. Compared to EM-800, EM-1538 is a safer, simpler, and easier salt to synthesize. In administering either EM-800 or EM-1538, it is believed to result in the same active compound in vivo.

Another preferred SERM is Lasoxifene (CP-336,156; (–)-cis-(5R,6S)-6-phenyl-5-[4-(2-pyrrolidin-1-yletoxy) phenyl]-5,6,7,8-tetrahydronaphthalen-2-ol, D-(–)-tartrate salt) (available from Pfizer Inc., USA).

Other preferred SERMs of the invention include Tamoxifen ((Z)-2-[4-(1,2-diphenyl-1-butenyl)]-N,N-dimethylethanamine) (available from Zeneca, UK), Toremifene (available from Orion-Farmos Pharmaceutica, Finland, or Schering-Plough), Droloxifene, and Raloxifene (Eli Lilly and Co., USA), Arzoxifene (LY 335563) and LY 353381 (Eli Lilly and Co., USA), Ospemifene (FC 1271) (available from Orion-Farmos Pharmaceutica, Finland), Iodoxifene (Smith-Kline Beecham, USA), Levormeloxifene (3,4-trans-2,2-dimethyl-3-phenyl-4-[4-(2-(2-(pyrrolidin-1-yl)ethoxy)phenyl]-7-methoxychroman) (Novo Nordisk, A/S, Denmark) which is disclosed in Shalmi et al. WO 97/25034, WO 97/25035, WO 97/25037, WO 97/25038; and Korsgaard et al. WO 97/25036), GW-5638 (described by Willson et al., 1997, Endocrinol, 138(9): 3901-3911), SERM 3339 in development by Aventis (France) and indole derivatives (disclosed by Miller et al. EP 0802183A1) and TSE-424 and ERA-923 developed by Wyeth Ayers (USA) and disclosed in JP10036347 (American home products corporation) and nonsteroidal estrogen derivatives described in WO 97/32837.

Any SERM used as required for efficacy, as recommended by the manufacturer, can be used. Appropriate dosages are known in the art. Any other non steroidal antiestrogen commercially available can be used according to the invention. Any compound having activity similar to SERMs (example: Raloxifene can be used).

SERMs administered in accordance with the invention are preferably administered in a dosage range between 0.01 to 10 mg/kg of body weight per day (preferably 0.05 to 1.0 mg/kg), with 10 mg per day, especially 20 mg per day, in two equally divided doses being preferred for a person of average body weight when orally administered, or in a dosage range between 0.003 to 3.0 mg/kg of body weight per day (preferably 0.015 to 0.3 mg/ml), with 1.5 mg per day, especially 3.0 mg per day, in two equally divided doses being preferred for a person of average body weight when parentally administered (i.e. intramuscular, subcutaneous or percutaneous administration). Preferably the SERMs are administered together with a pharmaceutically acceptable diluent or carrier as described below.

Preferred type 5 cGMPphosphodiesterase inhibitor are Sildenafil marketed under the Tradename "Viagra" by Pfizer USA, Tadalafil marketed under the Tradename "Cialis" by Eli Lilly USA, vardenafil marketed under the Tradename "Levitra" by Bayer (Germany). It is also preferred type 5 cGMPphosphodiesterase inhibitor which are presently in development: DA-8159 by Dong-A Pharm Tech (South Korean), EMR-62203 by Merck (Germany), TA-1790 by Tanabe Seiyaku (Japan), SCH-446132 by Schering-Plough (U.S.A.), and UK-371800 by Pfizer (U.S.A.).

One preferred prostaglandin is alprostadil marketed under the Tradename "Alprox-TD" by NexMed (USA).

With respect to all of the dosages recommended herein, the attending clinician should monitor individual patient response and adjust dosage accordingly.

EXAMPLE OF EFFICACY OF THE INVENTION

Example 1

Materials and Methods

Animals and Treatments

Ten to twelve week-old female Sprague-Dawley rats (Crl:CD® (SD)Br VAF/Plus™) (Charles River Laboratory, St-Constant, Canada) weighing approximately 220-270 g at start of the experiment were used. The animals were acclimatized to the environmental conditions (temperature: 22±3° C.; humidity: 50±20%; 12-h light-12-h dark cycles, lights on at 07:15 h) for at least one week before starting the experiment. The animals were housed individually and were allowed free access to water and rodent food (Lab Diet 5002, Ralston Purina, St-Louis, Mo.). The experiment was conducted in accordance with the CCAC Guide for Care and Use of Experimental Animals in an animal facility approved by the Canadian Council on Animal Care (CCAC) and the Association for Assessment and Accreditation of Laboratory Animal Care (AAALAC).

A total of 126 female rats were randomly distributed into 9 groups of 14 animals each as follows: 1) Intact control; 2) Ovariectomized control (OVX); 3) OVX+Acolbifene (2.5 mg/kg); 4) OVX+Premarin (0.5 mg/kg); 5) OVX+Premarin+Acolbifene; 6) OVX+DHEA (80 mg/kg); 7) OVX+DHEA+Acolbifene; 8) OVX+DHEA+Premarin; 9) OVX+DHEA+Acolbifene+Premarin. On the first day of the study, the animals of all groups (except group one) were bilaterally ovariectomized (OVX) under isoflurane-induced anesthesia. Premarin and Acolbifene were administered by oral gavage (0.5 ml/rat) as suspensions in 0.4% methylcellulose while DHEA in 50% ethanol-50% propylene glycol (0.5 ml/rat), was topically applied on a shaved area of 2×2 cm of the dorsal skin. Dosage selection for Premarin corresponds to the minimal dose sufficient to reverse OVX-induced uterine atrophy, while Acolbifene was administered at a dose sufficient to cause uterine atrophy similar to OVX after its administration to Premarin-treated OVX animals. The dose of DHEA used gave DHEA blood levels at 70-100 nmol/L. Treatments were initiated on day 2 of the study and the compounds were administered once daily for 36 weeks. Animals from the intact and OVX control groups received the vehicle alone.

Twenty-four hours after the last dosing, overnight fasted animals were sacrificed under isoflurane anesthesia by exsanguination at the abdominal aorta (9 animals per group) or by intracardiac perfusion with 10% neutral buffered formalin (5 animals per group). Vaginae from non-perfused animals were collected and weighed, while the vaginae collected from perfused animals were marked with black ink on the ventral side, and then trimmed as described below.

Histological Procedures

Figure 1:
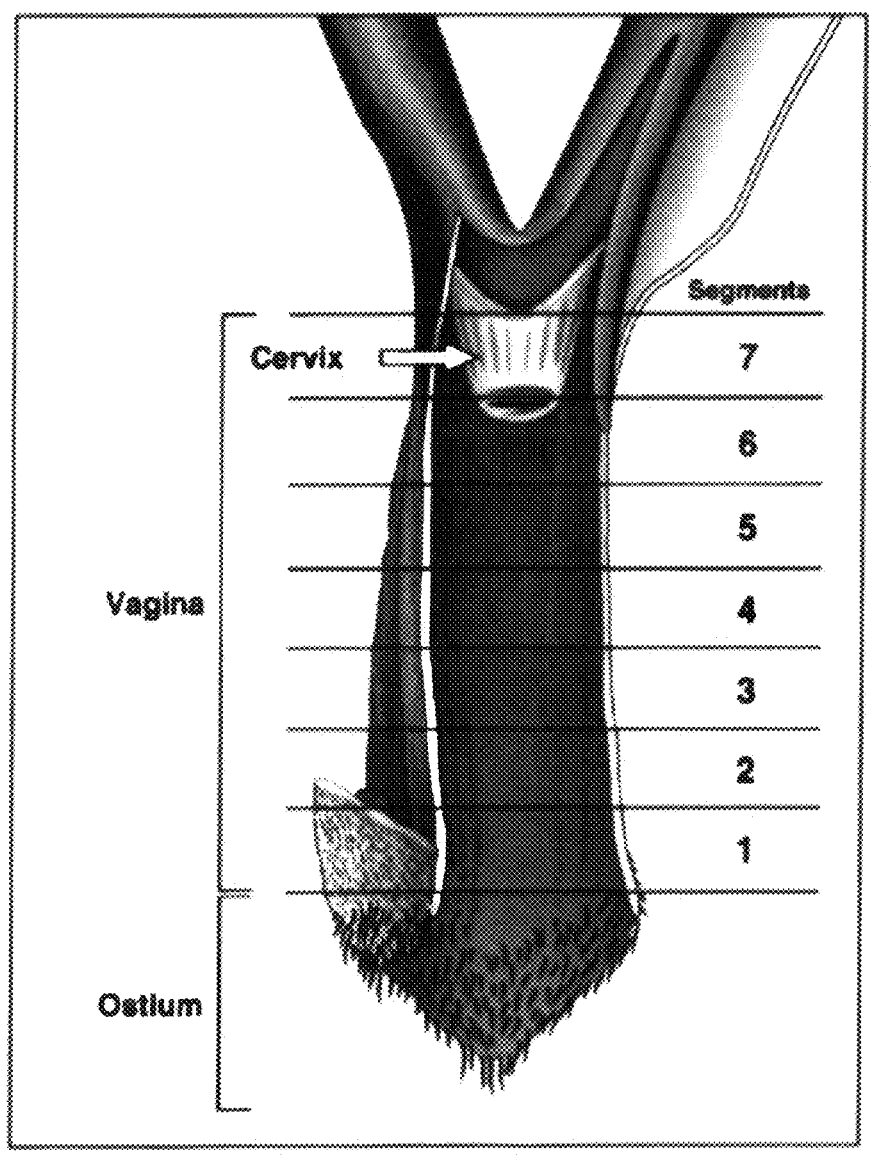
FIG. 1 shows the Division along the longitudinal axis of the rat vagina into seven cross-segments, from the external orifice (ostium) (segment 1) to the cervix level (segment 7) (portio vaginalis uteri).

The entire vagina of each perfused animal was post-fixed in 10% neutral buffered formalin. Each vagina was then divided into seven equal cross-segments as illustrated in FIG. 1, routinely processed and embedded altogether in the same paraffin block. Within the paraffin block, the seven vaginal cylindrical segments were positioned in a sequence corresponding to their original anatomical position and oriented perpendicular to the surface of the block, thus allowing the segments to be cut in cross-sections. For each animal, a 4 µm-thick paraffin section was cut and stained with haematoxylin-eosin for morphological examination.

Histomorphometry

Measurements of the different vaginal layers were performed on the fifth segment (FIG. 1), which is approximately halfway between the middle region and the portio vaginalis uteri (segment 7). This fifth segment was found to display a representative epithelial surface and a sufficient thickness of smooth muscle. Images were captured with a DC-330 3CCD color camera (Dage-MTI, Michigan City, Ind., USA) and quantified using Image-Pro Plus 3.0 software (Media Cybernetics, Silver Spring, Md., USA). Thus, using a ×5 objective (Leica Microsystems, Willowdale, Ont., Canada), 3 to 4 thickness measurements per layer were obtained from representative areas of the epithelium and muscularis, and for the three vaginal layers together. The total vaginal thickness, the thickness of the epithelium and the thickness of the muscularis were thus measured. The thickness of the lamina propria was obtained by subtracting the thickness of the epithelium and muscularis from total vaginal thickness.

Immunohistochemistry

Immunostaining was performed using Zymed SP kits (San Francisco, Calif.). Paraffin sections (4 µm) were deparaffinized in toluene and rehydrated through ethanol. Endogenous peroxidase activity was eliminated by preincubation with 3% $H_2O_2$ in methanol for 30 min. A microwave retrieval technique using citrate buffer (Tacha and Chen, 1994) was applied. After cooling the slides, non-specific binding was blocked using 10% goat serum for 20 min. Sections were then incubated for 1.5 h at room temperature with ERα (AB-1, Calbiochem, California), AR (N-20, Santa Cruz Biotechnology, California) or PR (Ab-4, NeoMarkers, California) antibodies, at 1:200, 1:250 and 1:250 respectively. After washing in PBS buffer, sections were incubated with biotinylated anti-rabbit secondary antibody for 10 min and thereafter with streptavidin-peroxidase for another 10 min. Diaminobenzidine was used as the chromogen to visualize the biotin/streptavidin-peroxidase complex, under microscope monitoring. Counterstaining was performed using #2 Gill's hematoxylin for 30 sec. For controls, immunoabsorption with an excess of the peptide used to raise the antibody, or substitution with non immune rabbit IgG, was performed. Semiquantitative evaluation of the number and intensity of immunostained nuclei was performed as indicated in Table 2.

TABLE 1

Histological evaluation of the epithelium, lamina propria and muscularis in the seven rat vaginal segments.

| Group | | Vaginal walls | Segment 1 | Segment 2 | Segment 3 | Segment 4 | Segment 5 | Segment 6 | Segment 7 |
|---|---|---|---|---|---|---|---|---|---|
| INTACT | Estrus | E | KS | KS | KS | KS | KS | KS | KS |
| | | L | $T^1$-$L^2$ | t-L | t-L | t-M | M-M | M-M | M-M |
| | | M | s | s | t | M | T | T | T |
| | proestrus | E | KS | MSM-KS | MSM | MSM | MSM-KS | MSM-KS | MSM-KS |
| | | L | T-M | t-M | t-M | t-M | t-M | M-M | M-M |
| | | M | s | s | t | M | M | T | T |
| OVX | Control | E | A | A | A | A | A | A | A |
| | | L | t-H | t-M | t-H | t-H | t-H | M-M | M-H |
| | | M | s | s | t | t | t | t | M |
| | Acolbifene | E | KS | SCM-A | SCM-A | SCM-A | SCM-A | SCM-A | SCM-A |
| | | L | M-M | t-M | t-H | t-H | t-H | t-H | M-H |
| | | M | s | s | s | s | t | t | t |
| | Premarin | E | KS | KS-MSM | KS-MSM | KS-MSM | KS-MSM | KS | KS |
| | | L | M-L | t-M | t-M | M-M | M-M | M-H | T-H |
| | | M | s | s | t | M | T | T | T |
| | Premarin + Acolbifene | E | KS | A-SCM | SCM-A | SCM-A | SCM-A | SCM-A | SCM-A |
| | | L | M-M | t-M | t-H | t-H | M-M | M-M | M-M |
| | | M | s | s | t | t | t | t | M |
| | DHEA | E | KS-LHM | LHM | LHM | LHM | LHM | LHM-SCM | LHM-SCM |
| | | L | M-H | t-H | t-H | t-H | t-H | M-H | M-H |
| | | M | s | s | s | t | M | M | M |
| | DHEA + Acolbifene | E | KS-LHM-SCM | SCM-LHM | SCM-LHM | SCM-LHM | SCM-LHM | SCM-LHM | LHM-SCM |
| | | L | M-M | t-M | t-H | t-H | M-H | M-H | M-H |
| | | M | s | s | s | t | t | M | M |

TABLE 1-continued

Histological evaluation of the epithelium, lamina propria and muscularis in the seven rat vaginal segments.

| Group | Vaginal walls | Segment 1 | Segment 2 | Segment 3 | Segment 4 | Segment 5 | Segment 6 | Segment 7 |
|---|---|---|---|---|---|---|---|---|
| DHEA + Premarin | E | KS | MSM-KS | MSM-KS | MSM-KS | MSM-KS | KS | KS |
|  | L | M-M | t-L | t-M | t-M | M-H | M-M | M-H |
|  | M | s | s | t | M | T | T | T |
| DHEA + Premarin + Acolbifene | E | KS | SCM-LHM-KS | SCM-LHM | SCM-LHM | SCM-LHM | SCM-LHM | LHM-SCM |
|  | L | M-M | M-H | t-H | M-H | t-H | M-H | M-M |
|  | M | s | s | s | t | M | M | M |

E = epithelium morphology: KS (keratinized stratified squamous), LHM (large hypertrophied mucous cells), SCM (small aligned columnar or cuboidal mucous cells), MSM (mixed stratified squamous overlaid by mucous cells), A (atrophy: small cuboidal cells).
Two different abreviations for a given segment indicate two different patterns and that the first one is the predominant.
[1]L = lamina propria thickness: T (thick), MT (moderately thick), t (thin);
[2]compactness of collagen fibers: H (high), M (moderate), L (low);
M = muscularis thickness: T (thick), MT (moderately thick), t (thin), s (scarce).

TABLE 2

Semiquantitative evaluation of the number and intensity of immunostained nuclei for AR, ER alpha and PR in the epithelium, lamina propria and muscularis in the fifth segment of the rat vagina.

|  |  | Sex steroid receptor | | | | | | | | |
|---|---|---|---|---|---|---|---|---|---|---|
|  |  | AR | | | ERα | | | PR | | |
|  |  |  |  |  | Vaginal layer | | | | | |
|  | Group | E | L | M | E | L | M | E | L | M |
| Intact | Estrus Reference of low ERα and high PR | 2++ | 2+++ | 1+ | 1+ | 1+ | 3+ | 2+++ | 3+++ | 3+++ |
|  | Diestrus Reference of high ERα and low PR | 3+++ | 3+++ | 3+++ | 3+++ | 1++ | 1+ | 0 | 2++ | 2++ |
| OVX | control | 1++ | 1+++ | 1+++ | 2++ | 1+++ | 1+++ | 0 | 0 | 0 |
|  | Acolbifene | 2++ | 1+++ | 1+++ | 0 | 0 | 0 | 0 | 0 | 0 |
|  | Premarin | 2++ | 2+++ | 1+ | 2++ | 3++ | 3++ | 2++ | 2+++ | 3+++ |
|  | Premarin + Acolbifene | 2++ | 1+ | 1+ | 0 | 0 | 0 | 0 | 0 | 0 |
|  | DHEA | 3+++ | 3+++ | 3+++ | 2++ | 2+++ | 3+++ | 0 | 0 | 1++ |
|  | DHEA + Acolbifene | 3+++ | 3+++ | 3+++ | 0 | 0 | 0 | 0 | 0 | 0 |
|  | DHEA + Premarin | 2+++ | 3+++ | 3+++ | 2+ | 2+++ | 3+++ | 2++ | 2+++ | 3+++ |
|  | DHEA + Premarin + Acolbifene | 3+++ | 3+++ | 3+++ | 0 | 0 | 0 | 0 | 0 | 0 |

Androgen receptor (AR),
estrogen receptor alpha (ERα),
progesterone receptor (PR),
epithelium (E),
lamina propria (L),
muscularis (M).
Numbers represent the semi-quantitative evaluation of labeled nuclei: 0 = none, 1 = low, 2 = moderate, 3 = high
Labeling intensity is indicated as low: +, moderate: ++ and high: +++

Statistical Analysis

Data are presented as means±SEM of 8-9 animals per group for vaginal weight or 5 animals per group for vaginal layer thickness determinations. Statistical significance was determined according to the multiple-range test of Duncan-Kramer (Kramer, 1956, Biometrics, 12: 307-310).

Results

Morphology and Thickness of the Different Layers of Rat Vagina

To examine with precision and detail the three layers of the rat vaginal wall, namely the epithelium, lamina propria and muscularis, seven segments obtained along the longitudinal axis (FIG. 1) were first examined. While important morphological differences were observed between the groups, in general, the differences were uniform in all animals of the same group and segments 2, 3, 4, 5, 6 and 7 have shown a similar epithelial morphology. The few exceptions observed will be mentioned later. Segment 5 was thus used to illustrate the effect of the various treatments on the vaginal epithelium.

Figure 3A:
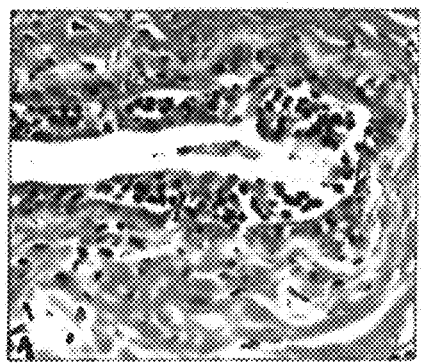
FIGS. 3A-3B show the vaginal mucosa of OVX animals.
Figure 3B:
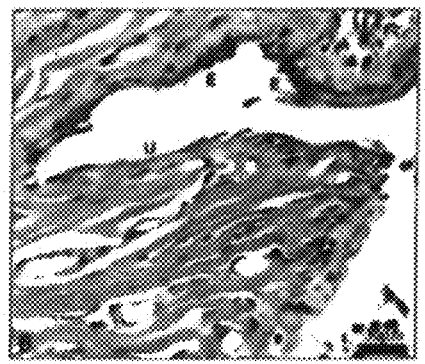
Figures 4A, 4B, 4C, 4D:
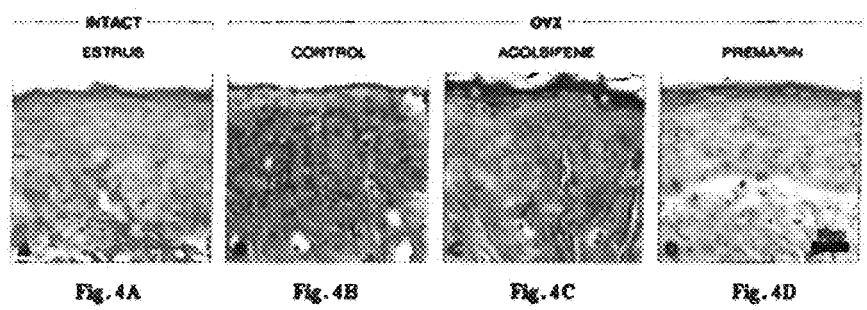
FIGS. 4A-4D illustrate the estrogen-like effect of Acolbifene on the vaginal epithelium lining of segment 1 (external opening). Comparisons with relevant groups are made. In intact rats at estrus Figure A and in Premarin-treated animals FIG. 4D, the epithelium is 10-15 layer-thick and keratinized. In OVX controls FIG. 4B, the epithelial thickness is reduced to 4-6 layers and is generally not keratinized (see the absence of stratum granulosum), while in Acolbifene-treated animals FIG. 4C, the thickness is restored to 9-11 layers and keratinized.

In the OVX group, the absence of ovarian stimulation led to an atrophy of the vaginal epithelium which characterized all segments (Table 1 and FIG. 2C) with the presence of some small mucous cell areas. Most importantly, moderate to severe inflammation with many foci of intraepithelial microabcesses (small areas of agglomerated leucocytes within the epithelium) were a frequent finding. These changes were frequently accompanied by focal erosion (zones where the epithelial layer partially disappears) and ulceration (complete disappearance of the epithelial layer) (FIG. 3).

In OVX animals treated with Acolbifene, segment 1 showed a keratinized stratified squamous epithelium similar to that of the intact group, except that it included 9-11 cell layers compared to the 10-15 layers found in animals at estrus or when OVX animals received Premarin (FIGS. 4A-4D). The epithelial thickness of Acolbifene-treated animals in segment 1 was thus higher than that of OVX rats, which comprised only 4-6 cell layers. In the other segments (Table 1), the basal layer was covered by a layer of low columnar mucous cells (FIG. 2D), which were more developed than in OVX animals. In the OVX+Acolbifene group, only three out of five animals showed signs of minimal inflammation while moderate to severe inflammatory changes were general findings in all OVX animals.

In all groups, segment 1 showed a comparable stratified squamous epithelium, except in the animals of the OVX group where atrophy was a predominant characteristic (FIG. 4). Moreover, in the OVX+DHEA and OVX+DHEA+Acolbifene groups, mucous cells frequently accompanied the dominant stratified squamous epithelium of segment 1 (not shown).

The seven segments of the vaginal epithelium of OVX animals which received DHEA were composed of large multilayered columnar mucous cells with distended cytoplasmic vacuoles, a feature typical of an androgenic effect (Table 1, FIG. 2G). Several large invaginations characterized the epithelium after DHEA treatment. A similar epithelial morphology was found in all segments of the OVX+DHEA+Acolbifene group, except that the size of the mucous cells and the number of their layers were decreased (Table 1, FIG. 2H). In the DHEA+PREMARIN-treated animals, a thick stratified epithelium of a "mixed" type composed of different ratios of squamous epithelium covered by layers of mucous cells (Table 1, FIG. 2I) was observed from the second to the fifth segment, thus revealing combined estrogenic and androgenic effects. In this group, three animals displayed mucification over the above-mentioned segments, while in the other two animals, a stratified squamous epithelium was observed in all segments (Table 1). When PREMARIN was combined with DHEA and Acolbifene, the epithelium was similar to that of the DHEA+Acolbifene group, thus indicating a blockade of the estrogen-induced squamous cell proliferation by Acolbifene (Table 1 and FIG. 2J).

The administration of DHEA to OVX animals increased thickness of the vaginal epithelium to 38±4 µm, while the addition of Acolbifene to DHEA did not change the epithelial thickness which remained at 37±5 man. When Premarin and DHEA were coadministered to OVX animals, a high thickness of 84±6 µm was observed, a value not significantly different from that of the group of animals which received Premarin alone. Finally, the combination of Premarin, DHEA and Acolbifene resulted in an epithelium of 32±3 µm-thick, a value similar to that of the groups which received DHEA alone or DHEA combined with Acolbifene.

Lamina Propria

Figure 6A:
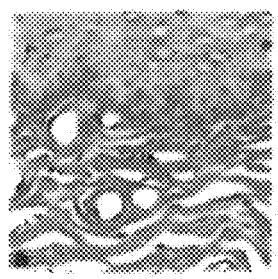
FIGS. 6A-6C show the compactness of collagen fibers of the lamina propria is in segment 5 illustrated as low (FIG. 6A), moderate (FIG. 6B), or high (FIG. 6C).
Figure 6B:
Figure 6C:
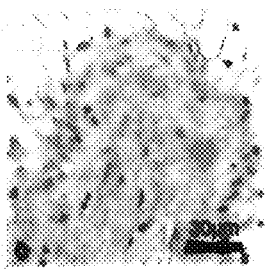

The degree of compactness of collagen fibers in the vagina was categorized as low, moderate and high (FIGS. 6A-6C, respectively), as observed in the area proximal to the epithelium. «Low» and «moderate compactness» were associated with the presence of coarse collagen fibers loosely or less loosely aggregated together, respectively, while «high compactness» was the term used to describe tightly packed fine collagen fibers, displaying a smooth, textured appearance. In all the animals, there were relatively few fibrocytes in proportion to the amount of collagen, and they appeared predominantly flattened and shrunken.

Careful examination of each animal (Table 1) reveals that, in general, the compactness of the collagen fibers in segment 1 is moderate (except low in rats at estrus and in Premarin-treated OVX animals, or high in OVX and DHEA-treated OVX rats), while increasing in compactness in segments 2 and 3 to reach a plateau that generally remains constant until segment 7. Thus, along the longitudinal axis of the vagina in intact rats at estrus, compactness of the collagen fibers was low in segments 1 to 3 and moderate in segments 4 to 7. Atrophy was often associated with increased compactness of collagen fibers in the OVX and OVX+Acolbifene groups (Table 1). In Premarin-treated OVX animals, compactness in segment 1 was low and moderate in segments 2 and 3, while in the other segments, compactness of the collagen fibers increased gradually to become high in segments 6 and 7.

Figure 5A:
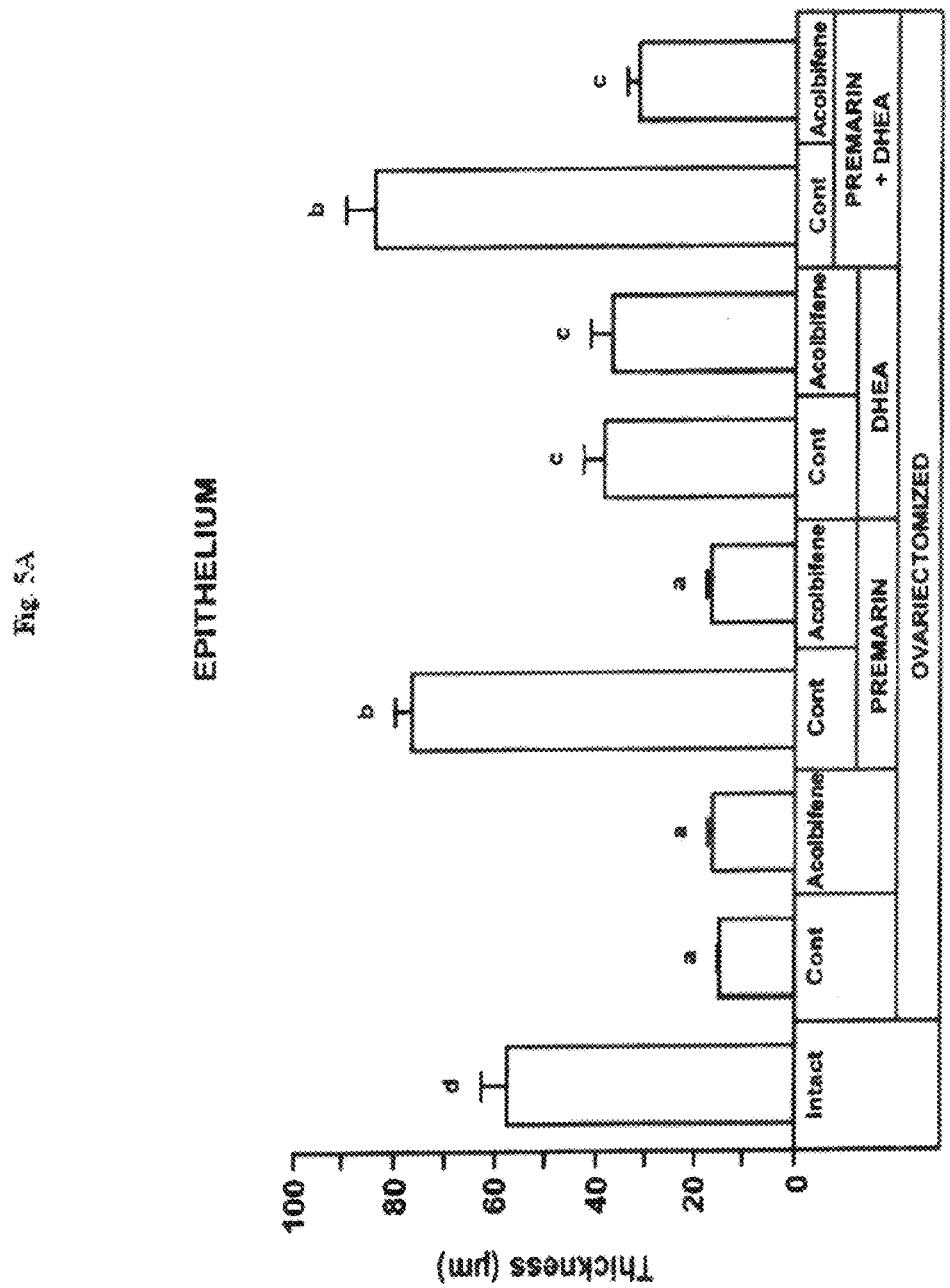
Figure 5B:
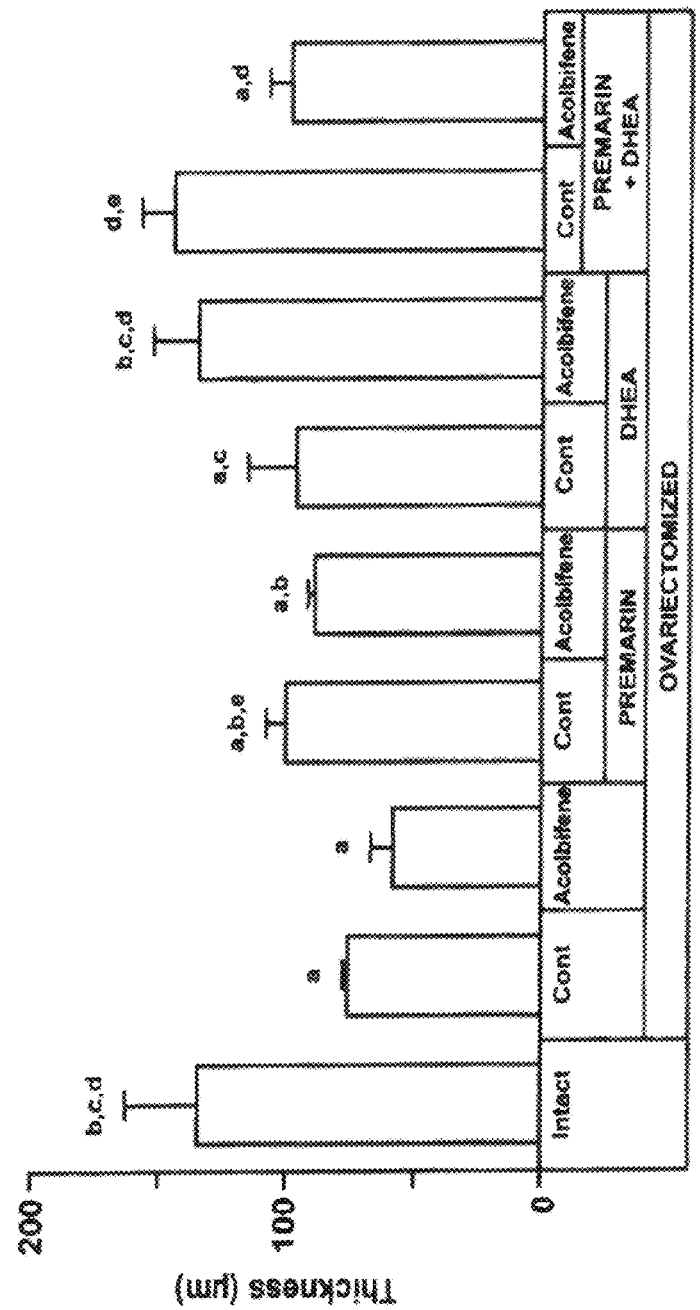
Figure 5C:
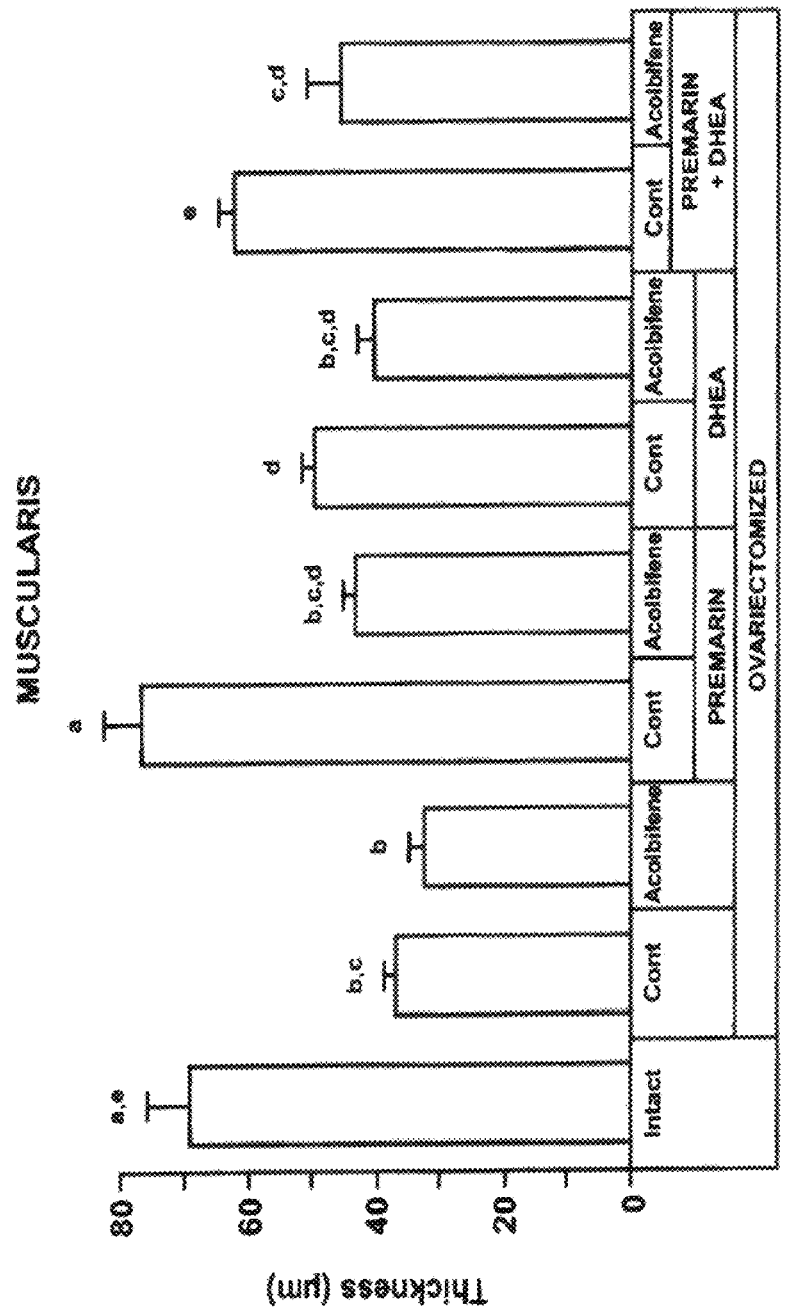

Visual light microscope examination of the lamina propria thickness along the vagina generally revealed that is was moderately thick in segment 1 while thinner in segments 2 to 4. In segments 5 to 7, the thickness increased progressively to a level similar to segment 1. The corresponding mean values of lamina propria thickness measured in segment 5 (FIG. 5B) indicate that OVX led to a significant decrease in lamina propria thickness (76±2 µm versus 135±28 µm in the intact group) with a non significant decrease induced by Acolbifene (60±8 µm). The increase observed after Premarin or Premarin+Acolbifene administration in OVX animals remained below the intact group (100±9 µm and 90±3 µm, respectively versus 135±28 µm). The administration of DHEA led also to a statistically non significant increase in lamina propria thickness (96±20 µm), and the addition of Acolbifene led to further increased thickness (136±17 µm), reaching that of intact animals. Treatment of OVX animals with Premarin+DHEA significantly increased the thickness, (144±14 µm) when compared to DHEA alone. Finally, the animals treated with Premarin+DHEA+Acolbifene displayed a thickness (99±9 µm) similar to that of the group treated with DHEA alone, and lower than that of the Premarin+DHEA group, although the difference was not statistically significant.

DHEA induced a moderate increase in muscularis thickness (50±2 µm), which was slightly decreased by the addition of Acolbifene (41±3 µm). Finally, treatment with Premarin and DHEA combined resulted in a notable thickness increase (62±3 µm), when compared to animals treated with DHEA alone. When Acolbifene was added to Premarin and DHEA, muscularis thickness decreased (46±5 µg) to a value comparable to DHEA and Acolbifene.

When total vaginal wall thickness was measured (FIG. 5D), the outer thin layer of connective tissue composing the adventitia was not included. OVX led to a marked (51%) vaginal wall atrophy (128±3 µm, versus 262±39 µm in the intact) and the addition of Acolbifene to OVX had no effect (108±8 µm) (FIGS. 7A, 7B and 7C). Premarin treatment maintained the total thickness to a value (253±10 µm) similar to that of intact animals while the addition of Acolbifene to Premarin reversed the effect of Premarin (150±4 µm) (FIGS. 7D and 7E, respectively). Total vaginal thickness achieved by DHEA treatment (184±21 µm) was about 25% lower than that of the Premarin alone-treated group (FIG. 7F). On the other hand, the addition of Acolbifene to DHEA led to a non significant thickness increase (213±20 µm), which became non significantly different from the intact group (FIG. 7G). Finally, coadministration of Premarin and DHEA to OVX animals markedly increased the thickness (290±13 µm) to a value similar to that of intact animals (FIG. 7H). The addition of Acolbifene to DHEA and Premarin reversed the effect to a value (176±11 µm) not significatively different from DHEA alone (FIG. 7I).

Vaginal Weight

Figure 8:
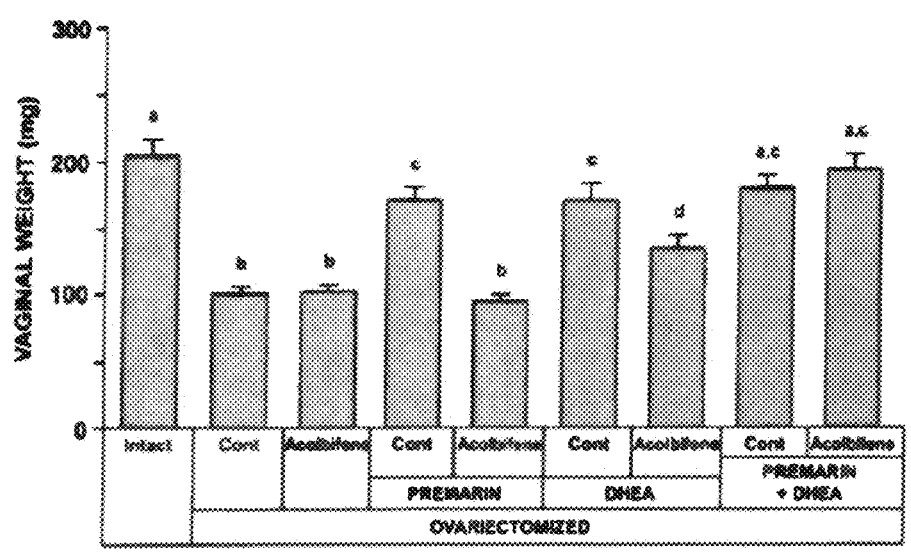
FIG. 8 shows the vaginal weight measured 36 weeks after OVX and treatment of OVX animals with Acolbifene, Premarin and DHEA alone or in combination. Intact animals are added as controls.
Figure 9:
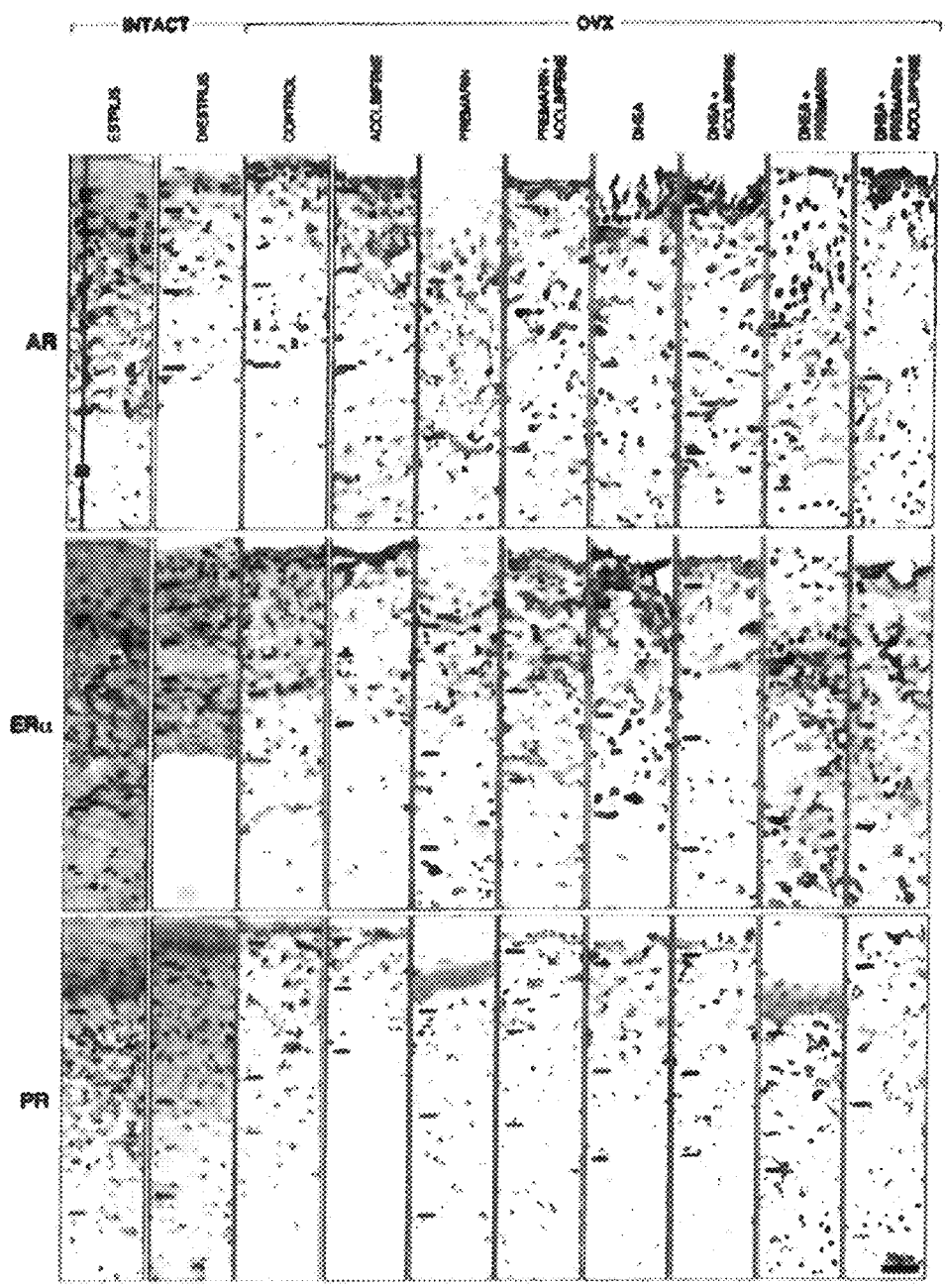
FIG. 9 shows the Immunohistochemical localization of AR, ERα and PR in the (E) epithelium, (L) lamina propria and (M) muscularis at the level of the fifth vaginal segment of the different groups. The bars indicate the separation between the three vaginal compartments.
Figures 11A, 11B, 11C:
FIGS. 11A-11C show a comparison of indicated rat vaginal epithelial morphology following treatment with each of three different SERMs.
Figure 12:
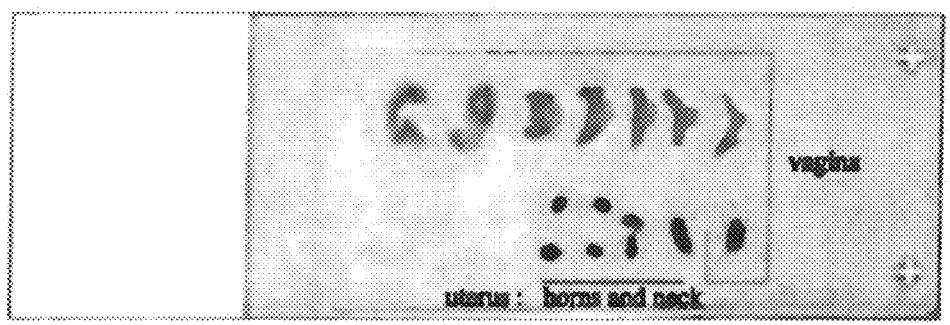
FIG. 12 shows the picture of a microscope slide to display the positioning of the 8 vaginal segments (the whole upper row and the section at the right-down corner), followed by the 4 uterine segments (1 segment of uterine neck and 3 segments of the two uterine horns—2 sections per horn) in a sequence corresponding to their original anatomical position. Segment 8 includes the lateral vaginal folds neighbouring the beginning of the uterine cervix.

After eight months of treatment, the changes observed in vaginal weight between the different groups (FIG. 8) generally follow the above-described morphological observations. Indeed, vaginal weight after OVX decreased by about 50% (101±5 mg) compared to the intact group (205±11 mg) while treatment of OVX animals with Acolbifene alone had no effect on vaginal weight. On the other hand, administration of Premarin led to a vaginal weight increase that did not yet reach the value of intact animals (170±9 mg) while the addition of Acolbifene to Premarin reversed the estrogen-induced weight gain to a value similar to that of OVX animals (96±4 mg). Conversely, when DHEA was given to OVX animals, vaginal weight increased to a value (171±12 mg), similar to that of the Premarin-treated group, and the combination of Acolbifene and DHEA resulted in a decrease in weight (135±9 mg), which remained above that of the OVX group. Finally, coadministration of Premarin and DHEA in OVX animals resulted in a vaginal weight gain (179±10 mg) reaching a value similar to those of the OVX+DHEA and OVX+Premarin groups. The addition of Acolbifene to this combination had no significant effect (194±12 mg).

DHEA treatment of OVX animals led to the strong labeling or AR of many nuclei in the three vaginal layers, the same pattern being found when the combinations of DHEA+Acolbifene and DHEA+Premarin were used, with the exception of a smaller number of labeled nuclei in the superficial layers of the epithelium in the latter group. The combination of DHEA, Premarin and Acolbifene also resulted in a strong staining of the majority of the nuclei in the three vaginal wall layers.

Discussion

Vaginal dryness or atrophic vaginitis, also referred to as urogenital atrophy, with sexual dysfunction is a common problem in postmenopausal women (Notelovitz, 2000, Menopause, 7(3): 140-142). The most common symptoms are dryness, burning, pruritus, irritation and dyspareunia, thus leading to decreased libido and quality of life (Berman et al., 1999, Curr Opin Urol, 9(6): 563-568). Since estrogen loss is known to be involved, estrogen replacement therapy (ERT) and HRT are the treatments of choice. However, as new information on sex steroid physiology in women strongly suggests an important role of androgens (Labrie et al., 2003, End Rev, 24(2): 152-182), the present study compares the overall hormonal effects of an alternative to HRT or ERT, namely DHEA alone or in association with the pure antiestrogen Acolbifene and also with Premarin on rat vaginal morphology and sex steroid receptor expression. DHEA was administered percutaneously to avoid first pass through the liver (Labrie et al., 1996, Endocrinol, 150: S107-S118).

Finally, our results have shown a significant vaginal weight increase with Premarin treatment, when compared to OVX animals, the value being similar to that observed in DHEA-treated group. It is appropriate to recall that, although vaginal and uterine weight increases in rodents are commonly used as measures of estrogenicity, these organs can also respond to progesterone and testosterone, among other compounds (Emmens and Martin, 1964, Dorfman Ed, Ed Academic Press NY: 1).

In the potential triple combination, the equine estrogen Premarin is aimed at acting in the brain to relieve the vasomotor symptoms. In fact, the benefits of co-administration of the pure selective antiestrogen Acolbifene with an estrogen in order to neutralize the unwanted peripheral effects of the estrogen have been well described by Labrie et al. (Labrie et al., 2003, Endocrinol, 144 (11): 4700-4706). In the present study, when Acolbifene was given to OVX animals, the most typical morphological feature induced by the SERM was the appearance of a superficial layer of well-aligned small mucus cells overlying a basal cell layer, a pattern which was slightly more pronounced in the Premarin+Acolbifene group and which remained preponderant in all groups treated with Acolbifene, including when the SERM was added to DHEA. Vaginal epithelium mucification under treatment with an antiestrogen has been reported in immature (Anderson and Kang, 1975, Am J anat, 144(2): 197-207) and adult (Yoshida et al., 1998, Cancer Lett, 134(1): 43-51) rats. Although this morphological pattern has been compared to the progesterone-induced mucification (Anderson and Kang, 1975, Am J anat, 144(2): 197-207), the molecular mechanism by which an antiestrogen induces epithelial mucification remains unknown.

Many beneficial effects of DHEA have been reported in postmenopausal women (Labrie et al., 1997, J. Clin. Endocrinol. Metab., 82: 3498-3505; Labrie et al., 1991, Mol Cell Endocrinol, 78: C113-C118). Since no specific receptor for DHEA has been characterized, the morphological changes observed in the rat vagina after DHEA treatment reflect its intracrine conversion into active sex steroids having androgenic and/or estrogenic action through intracrine mechanisms (Labrie et al., 1991, Mol Cell Endocrinol, 78: C113-C118). Those changes comprise intense epithelial mucification, high compactness of delicate, finely woven lamina propria collagen fibers and moderate muscularis thickness increase when compared to OVX animals. The two first morphological changes are typical of androgenic effects while the third shows an estrogen-like activity, which is further supported by a concomitant increase in progesterone receptor expression in the muscularis layer.

Since DHEA is transformed into either or both androgens and estrogens in peripheral tissues, the thick mucified multilayered epithelium observed in the present study after treatment of OVX animals with DHEA, suggests a predominant androgenic effect of mucification in the rat vagina, an effect which could mask any potential coexisting minor estrogenic effect at the epithelial level. A previous study has shown the same mucification effect in the rat vagina (Sourla et al., 1998, J Steroid Biochem. Mol. Biol., 66(3): 137-149); In that previous study, the intravaginal application of DHEA achieved a significant effect at a dose ten times lower than that found to be active following application of DHEA on the dorsal skin.

The present data indicate co-existing major androgenic and minor estrogenic actions of DHEA in the rat vagina. Moreover, the present results are well supported by the observation of the vaginal epithelium of OVX animals which received the same topical application of DHEA than that used in our study, plus a subcutaneous dose of the antiandrogen Flutamide (FLU) (unpublished results). Indeed, the androgenic effect of mucification produced by the androgenic component of DHEA was completely reversed by FLU and resulted in a stratified squamous epithelium, typical of an estrogenic effect (data not shown). If DHEA would have an exclusive androgenic effect (mucification) in the rat vagina, this effect would be reversed by FLU and an atrophic epithelium similar to that of OVX animals should then be observed. Previous studies in gonadectomized male and female rats have clearly established that treatment with DHEA leads to stimulatory androgenic and/or estrogenic effects on the prostate, seminal vesicle and uterus, depending upon the target tissue under investigation (Labrie et al., 1988, Endocrinol, 123: 1412-1417).

The combination of DHEA+Acolbifene, on the other hand, shows a reduction in the extent of epithelial mucification, thus displaying the alternance of a well-aligned mucus cell layer—an Acolbifene effect—and invaginations of multilayered hypertrophied mucous cells, which correspond to the androgenic effect of DHEA. Accordingly, Acolbifene inhibits the partial estrogenic effect of DHEA, while the major androgenic counterpart of DHEA is maintained and a small estrogen-like effect of Acolbifene is added, the latter being best seen at the ostium level. The vaginal weight decrease observed after the addition of Acolbifene to DHEA is smaller than that obtained after addition of Acolbifene to Premarin, thus illustrating the smaller estrogenic component of DHEA which is reversed by the antiestrogen, while the major androgenic component is not affected. In addition, the increases in lamina propria thickness and in compactness of the collagen fibers, when compared to those of OVX and intact animals respectively, in the DHEA+Acolbifene group, suggest, again, a potential role of androgens in increasing collagen compactness and thickness, since the estrogenic component of DHEA is blocked by Acolbifene.

Other studies have demonstrated that the action of DHEA in the rat mammary gland (Sourla et al., 1998, Endocrinol, 139: 753-764), skin sebaceous glands (Sourla et al., 2000, J Endocrinol, 166(2): 455-462) and bone mineral density (Martel et al., 1998, J Endocrinol, 157: 433-442) is almost exclusively androgenic. Nevertheless, the presence of an estrogenic action of DHEA in the rat vagina has been previously demonstrated through induction of vaginal opening and precocious ovulation in immature rats treated with this compound, while DHT, an androgen not aromatizable to estrogens, did not produce such effects (Knudsen and Mahesh, 1975, Endocrinol, 97(2): 458-468). The capacity of rat vaginal tissue to aromatize androgens, especially Testo, is likely to account for the major part of the estrogenic effect of DHEA in this organ (Lephart et al., 1989, Biol Reprod, 40(2): 259-267). Androst-5-ene-3p, 17-diol (5-diol), a DHEA metabolite known to bind the estrogen receptor (Shao et al., 1950, J Biol Chem, 250: 3095-3100; Poortman et al., 1975, J Clin Endocrinol Metab, 40(3): 373-379; Van Doom et al., 1981, Endocrinol, 108: 1587-1594; Adams et al., 1981, Cancer Res, 41: 4720-4726), could also contribute to the estrogenic effect (Poulin and Labrie, 1986, Cancer Res, 46: 4933-4937). The proposed combination of the antiestrogen Acolbifene with DHEA would thus prevent any unwanted stimulatory effect of 5-diol. On the other hand, acolbifene would show additional benefits by preventing bone loss (Martel et al., 2000, J Steroid Biochem Mol Biol, 74 (1-2): 45-56).

To the best of our knowledge, no previous study has shown the stimulatory effects of DHEA on the compactness and morphology of the lamina propria's collagen fibers and, to a lesser extent, on the muscularis. Such actions of DHEA-derived androgens and estrogens could have beneficial effects on vaginal function in postmenopausal women and should provide the substrates required for the action of inhibitors of type 5 phosphodiesterase such as sildenafil or tadalafil, possibly via androgen or estrogen-induced endothelial nitric oxide synthase (eNOS)-mediated facilitation of vaginal smooth muscle relaxation (reviewed in Munarriz et al., 2003, J Urol, 170 (2 Pt 2): S40-S44, Discussion S44-S45). In fact, Acolbifene has been found to induce eNOS in human and rat endothelial cells (Simoncini et al., 2002, Endocrinol, 143(6): 2052-2061).

The results obtained in all the groups involving DHEA treatment reveal that AR expression is up-regulated by the androgens derived from the intracrine transformation of DHEA in the rat vagina, in a similar fashion in the three tissue compartments.

The beneficial morphological changes, observed concomitantly with the strong modulation of rat vaginal AR by androgens, suggest that decreased serum levels of DHEA-derived androgens in postmenopausal women could contribute to the decreased vaginal health and eventually to the loss of libido and sexual enjoyment observed in this age group. Decreased serum total Testo, free Testo and DHEA-S were indeed found in women who consulted for decreased sexual desire (Guay and Jacobson, 2002, J Sex Marital Ther, 28 Suppl 1: 129-142).

In the present study, we have shown that treatment of OVX female rats with DHEA or the combination of DHEA with Acolbifene and of DHEA with Acolbifene and Premarin reversed the OVX-induced atrophic changes found in the vagina through a predominant androgenic effect, via AR, which was reflected by intense epithelial mucification and increased compactness of the collagen fibers in the lamina propria. Treatment with DHEA alone also moderately increased muscularis thickness. Such data underline the importance of sex steroids synthesized locally from DHEA and DHEA-S in peripheral target tissues. In addition to these beneficial effects, Acolbifene reduced the inflammation incidence, possibly through an estrogen-like induction of a protective keratinized squamous epithelium at the ostium level and an antiestrogenic effect of mucification at the internal level.

Various attempts have been made to solve the problem of vaginal dryness, often linked to dyspareunia and loss of sexual enjoyment. As an example, local vaginal estrogen preparations are often prescribed to provide relief but the endometrium may be stimulated by the unopposed estrogen (Mattson et al., 1989, Maturitas, 11: 217-222). In hysterectomized postmenopausal women, ERT is still used but with the well-known increased risk of developing breast cancer. Moreover, ERT decreases serum androgen levels by increasing sex hormone binding globulin, which may induce a relative ovarian and adrenal androgen deficiency, thus creating an additional rationale for concurrent physiologic androgen replacement (Casson et al., 1997, Obstet Gynecol, 90(6): 995-998).

Example 2

Methods

Animals and Treatment

Ten to twelve week-old female Sprague-Dawley rats (Crl:CD(SD)Br) (Charles River Laboratory, St-Constant, Canada) weighing 215-265 g at time of ovariectomy were used. The animals were housed individually in an environmentally-controlled room (temperature: 22±3° C.; humidity: 50±20%; 12-h light-12-h dark cycles, lights on at 07:15 h). The animals were allowed free access to tap water and a certified rodent feed (Lab Diet 5002 (pellet), Ralston Purina, St-Louis, Mo.). The experiment was conducted in an animal facility approved by the Canadian Council on Animal Care (CCAC) and the Association for Assessment and Accreditation of Laboratory Animal Care (AAALAC) in accordance with the CCAC Guide for Care and Use of Experimental Animals.

Different experiments were performed: two 20-day and two 8-month studies. In each of the two first experiments, the animals were randomly distributed between 3 groups of 13 or 14 animals as follows: 1) Intact control; 2) Ovariectomized (OVX) control; 3) OVX+raloxifene (0.5 mg/kg), or, 3) OVX+LY 363381 (0.5 mg/kg). In one 8-month study, the animals were randomly distributed between 5 groups of 7-8 animals as follows: 1) Intact control; 2) Ovariectomized (OVX) control; 3) OVX+Acolbifene (0.5 mg/kg); 4) OVX+ERA-923 (0.5 mg/kg); 5) OVX+TSE-424 (0.5 mg/kg). In the other 8-month study, the animals were randomly distributed between 3 groups of 10-11 animals as follows: 1) Intact control; 2) Ovariectomized (OVX) control; 3) OVX+lasofoxifene (0.5 mg/kg). On the first day of the study, the animals of the appropriate groups were bilaterally ovariectomized (OVX) under isoflurane anesthesia. The tested compounds were then given once daily by oral gavage as a suspension in 0.4% methylcellulose (0.5 ml/rat) from day 1 to day 20 of the study or from day 1 to week 32 of the study.

Twenty-four hours after the last dosing, the animals were sacrificed under isoflurane anesthesia by exsanguination. The vaginae were collected and immersed in 10% neutral buffered formalin immediately after resection. The vaginae were then either cut in 7 cross-segments (for Acolbifene, ERA-923 and TSE-424) or cut to sample only the middle cross-segment. (raloxifene, lasofoxifene or LY 363381). The segments were then routinely processed and embedded in paraffin blocks. When appropriate, all the segments were positioned in the paraffin block in a sequence corresponding to their original anatomical position and oriented perpendicular to the surface of the block, thus allowing the segments to be cut in cross-sections. For each animal, a 4 µm-thick paraffin section was cut and stained with haematoxylin-eosin for morphological examination.

In FIGS. 10A-10H and FIGS. 11A-11C is shown a comparison between different SERMs: vaginal epithelium morphology, in the OVX rat, at magnification 200×. FIGS. 10A-10D show the epithelial morphology of the first segment of the vagina (ostium). While the epithelium of the OVX animals is thin (4-6 cell layers), atrophic and does not display a visible granular layer in FIG. 10A, the same epithelium is thicker in the 3 SERMs (8-11 cell layers) and displays a multilayered granular compartment, in FIGS. 10B, 10C and 10D. In FIGS. 10E-10H and FIGS. 11A-11C, a segment situated in the middle of the vagina is illustrated. In the OVX animals, the vaginal epithelium is thin and atrophic (2-3 cell layers), in FIG. 10E, while the thickness is increased in all the treated groups (FIGS. 10F-10H and FIGS. 11A-11C), due to the presence of one (Acolbifene, ERA-923 and TSE-424) or many (raloxifene, lasofoxifene or LY 363381) mucous cell layer(s) overlying the basal cell layer.

Example 3

Materials and Methods

Ten to twelve week-old female Sprague-Dawley rats (Crl:CD® (SD)Br VAF/Plus™) (Charles River Laboratory, St-Constant, Canada) weighing approximately 250-275 g at start of the experiment were used. The animals were acclimatized to the environmental conditions (temperature: 22±3° C.; humidity: 50±20%; 12-h light-12-h dark cycles, lights on at 07:15 h) for at least one week before starting the experiment. The animals were housed individually and were allowed free access to water and rodent food (Lab Diet 5002, Ralston Purina, St-Louis, Mo.). The experiment was conducted in accordance with the CCAC Guide for Care and Use of Experimental Animals in an animal facility approved by the Canadian Council on Animal Care (CCAC) and the Association for Assessment and Accreditation of Laboratory Animal Care (AAALAC).

A total of 25 female rats were randomly distributed into 5 groups as follows: 1) Three ovariectomized untouched control (OVX); 2) Four OVX+placebo suppository; 3) Six OVX+0.33 mg DHEA suppository; 4) Six OVX+0.66 mg DHEA suppository; 5) Six OVX+1.00 mg DHEA suppository. On the first day of the study, the animals of all groups were bilaterally ovariectomized (OVX) under isoflurane-induced anesthesia. The insertion into the vagina of one suppository began on day 5 of the study and was continued once daily until day 18 of the study, for a total of 14 days of treatment. The suppository was gently placed in the vaginal opening and then delicately pushed about 2-3 mm inside the vagina with the help of a small, smooth glass stick, disinfected in 70% alcohol and dried between each animal.

Twenty-four hours after the last dosing, the animals were sacrificed under isoflurane anesthesia by exsanguination. Vagina—including the urethra—and uterus were collected, and then trimmed as described below. For further analysis, two pieces of inguinal mammary gland were sampled, as well as a square piece of about 2×2 cm of shaved dorsal skin, the latter being put and gently flattened on a piece of carton.

Preparation of the Suppositories

DHEA suppositories were prepared using Whitepsol H-15 base (Medisca, Montreal, Canada). Any other lipophilic base such as Fattibase, Wecobee, cocoa butter, theobroma oil or other combinations of Whitepsol bases could also be used. The proper amounts of DHEA were weighed to give final concentrations of 0.33 mg or 0.66 mg or 1.00 mg per suppository of a final volume of 50 µl±3 µl. The proper amount of suppository base pellets to weight in order to obtain the final volume needed was calculated based on the previously measured density of the suppository base, which was 47.5 mg per 50 µl. The suppository base was put in a small beaker, melted in microwave at power 50% for about 3 min and 30 sec and then transferred on a heating plate, which was adjusted at the lowest power in order to keep the suppository base at a temperature of 50±3° C. The DHEA micronized powder (obtained from Scheweizerhall Inc. at a purity of 100%) was then added in the base, all at once, the whole clump left to sink and to wet for 3 min before being meticulously and slowly crushed and dissolved with a smooth rounded-end glass rod. Finally, the base with the dissolved DHEA (the placebo was the base without DHEA)

was poured, using a 1000 μl-Gilson pipette with a pre-heated pipette tip, in tube racks containing a series of 50 μl-moulds. These moulds were made from microcentrifuge tubes, each of them previously calibrated with 50 μl of water and cut at the level of the line drawn at the water surface. After 30 min of cooling at room temperature, the suppositories were put at 4° C. for another 30 min. Finally, the excess of base was trimmed with a razor blade and the suppositories were removed from their moulds and stored in closed glass bottles at 4° C. until use. They were allowed to reach room temperature before being applied to the animals.

Histological Procedures

The organs were immersed in 10% neutral buffered formalin immediately after resection. Each vagina and uterus was divided into 8 equal cross-segments and 4 cross-segments including two from the cervix and two from each of the two proximal and distal horns, respectively. The segments were then routinely processed and embedded all together in the same paraffin block. Within the paraffin block, all the segments were positioned in a sequence corresponding to their original anatomical position and oriented perpendicular to the surface of the block, thus allowing the segments to be cut in cross-sections. For each animal, a 4 μm-thick paraffin section was cut and stained with haematoxylin-eosin for morphological examination.

Results

Morphology of the Epithelium

After examination of all vaginal segments, it was found that segments 4 and 6 are representative to compare between treatments. Segment 4 was the most proximal to the ostium which did not display features of the external skin, and was not or to a lesser extent affected by the slight to moderate inflammatory changes usually found in the external area of the vaginal mucosa in control animals. Segment 6 represented the deeper vaginal mucosa and is separated from the uterine cervix by only one segment.

In general, the ventral side of the vagina displays a thicker and a more mucified epithelium when compared to the dorsal side.

Intact

At estrus, which is under major estrogenic influence, the vaginal epithelium is thick and keratinized. It displays from 12 to 18 cell layers in segment 4 (FIG. 13A), and 12 to 15 layers in segment 6 (FIG. 13C). Contrary to the thick stratified squamous epithelium seen at the ostium, the granular layers are not obvious in the internal vaginal epithelium. At metestrus, under minimal hormonal influence, the vaginal epithelium is thinner. It displays 6 to 10 cell layers in segment 4 (FIG. 13B), and 5 to 7 layers in segment 6 (FIG. 13D).

Ovariectomized Untouched

In segment 4 (FIG. 14A), the vagina is lined by a squamous stratified epithelium of 2 to 6 cell layers. The thickness of this segment is quite variable between animals. In segment 6 (FIG. 14B), complete atrophy is observed, with 2 to 3 cell layers of flat cells. Some rare foci of small cylindrical mucous cells could be seen throughout the whole vagina of these animals. Of the three animals of this group, two displayed mild inflammatory changes in the external three segments.

Placebo

In comparison with the OVX untouched group, the vaginal squamous stratified epithelium of the placebo group was slightly thicker, with segment 4 (FIG. 15A), displaying 4 to 8 cell layers. However, in segment 6 (FIG. 15B), the same morphology found in the OVX untouched group was observed, with 2-3 epithelial cell layers. As in OVX untouched animals, foci of small cylindrical mucous cells could be found throughout the vagina, slightly more when compared with the OVX untouched animals. Of the four animals of this group, three displayed mild inflammatory changes in the external three segments.

DHEA 0.33 mg/Suppository

In general, at low doses, the morphological effect of DHEA is characterized by well-aligned cylindrical mucous cells, while at higher doses, the mucous cells enlarge (hypertrophy), vacuolate and pile up. In the present group, the effect of DHEA is slightly discernible in segment 2 and gradually increases in segments 3-4, where there is an alternance of well-aligned and hypertrophied mucous cells. The DHEA effect slowly decreases in segments 5 and 6 where almost only well-aligned mucous cells can be observed. The effect becomes very little in segment 7 and disappears in the lateral vaginal folds of segment 8 (which includes the beginning of the cervix). Thus, in segment 4 (FIG. 16A), the vaginal epithelium is stratified squamous with 3 to 7 cell layers. About 20 to 60% of the vaginal lining consists of well-aligned mucous cells in alternance with 15 to 50% hypertrophied mucous cells, overlying one or more squamous stratified epithelium layers, and with non-mucified areas. In segment 6 (FIG. 16B), the epithelial thickness is reduced to almost the thickness found in OVX untouched animals. It consists of a squamous stratified epithelium of 2 to 5 cell layers, covered by a layer of well-aligned mucous cells. A large variation in the occurrence of mucous cells was observed, these cells covering from 5 to 75% of the vaginal surface, in alternance with non-mucified areas. Of the six treated animals, four of them displayed mild inflammation, unevenly distributed over the whole vagina.

DHEA 0.66 mg/Suppository

In this group, the effect of DHEA is discernible in segment 2 and increases significatively in segments 3-4 and 5 where a majority of hypertrophied mucous cells are observed. The number of hypertrophied mucous cells decreases in segments 6 and 7 where the majority of cells are well-aligned mucous cells. Thus, in segment 4 (FIG. 17A), the stratified squamous epithelium is 3 to 6 cell layer-thick. About 5 to 20% of the vaginal lining consists of well-aligned mucous cells in alternance with 10 to 75% of hypertrophied mucous cells, overlying one or more squamous stratified epithelium layers. Non-mucified epithelial areas are also present. In segment 6 (FIG. 17B), the epithelial thickness is reduced and consists of a squamous stratified epithelium of 2 to 4 cell layers, surmounted by a layer of well-aligned mucous cells. The amount of mucified areas varied from 20 to 80% of the vaginal surface, in alternance with non-mucified areas. Of the six treated animals, two displayed mild inflammation in the three external segments.

DHEA 1.00 mg/Suppository

In this group, the effect of DHEA is also discernible in segment 2, but it increases significatively in segments 3-4 and 5 where the vast majority of hypertrophied mucous cells are observed, and very slowly decreases in segments 6-7 and 8, where the vast majority of well-aligned mucous cells are observed. Thus, in segment 4 (FIG. 18A), the stratified squamous epithelium displays 3 to 9 cell layers. Hypertrophied mucous cells overlying 3 to 4 squamous cell layers cover 50 to 70% of the vaginal surface, while well-aligned mucous cells cover 5 to 30% of the vaginal surface. Non-mucified areas are interspersed between mucified cells. In segment 6 (FIG. 18B), the epithelial thickness is also reduced and consists of 2 to 4 cell layers. Hypertrophied mucous cells overlying 1 to 3 squamous cell layers cover about 30 to 100% of the vaginal surface while well-aligned mucous cells cover 0 to 70%. Few interspersed non-mucified areas are also observed. Of the six treated animals, four of them displayed mild inflammation in the four external segments.

Conclusions

1. The vehicle used for rat intravaginal treatment has desirable characteristics:
   a. Easily prepared in calibrated mould;
   b. Excellent capability to completely dissolve the DHEA micronized powder, thus assuring a standardized dosage;
   c. No significant tissue reaction and morphological alterations of the vaginal mucosa: only a slight thickness increase of the epithelium was observed in the first 3 to 4 segments, possibly due to the manipulations accompanying the insertion of the suppository.
2. DHEA produced an effect on the vaginal epithelial morphology at the lowest tested dose (0.33 mg/suppository). The effect is maximal from the $3^{rd}$ to the $5^{th}$ segment, then decreases gradually to disappear at the level of the $7^{th}$ segment.
3. At the DHEA dose of 0.66 mg/suppository, the effect is also present at the $3^{rd}$ segment and remains quite strong in the $6^{th}$ segment.
4. At the DHEA dose of 1.00 mg/suppository, the effect is strong from segment 2-3 to the deep vaginal folds neighbouring the uterine cervix.

Pharmaceutical Composition Examples

Set forth below, by way of example and not of limitation, are several pharmaceutical compositions utilizing preferred active SERM Acolbifene, preferred active sex steroid precursor DHEA, preferred estrogen 17β-estradiol or premarin, preferred type 5 cGMP phosphodiesterase inhibitor Sildenafil or Tadalafil. The concentration of active ingredient may be varied over a wide range as discussed herein. The amounts and types of other ingredients that may be included are well known in the art.

Example A

Tablet

| Ingredient | Weight % (by weight of total composition) |
| --- | --- |
| DHEA | 15.0 |
| Gelatin | 5.0 |
| Lactose | 63.5 |
| Starch | 16.5 |

Example B

Gelatin Capsule

| Ingredient | Weight % (by weight of total composition) |
| --- | --- |
| DHEA | 15.0 |
| Lactose hydrous | 70.0 |
| Starch | 4.8 |
| Cellulose microcrystalline | 9.8 |
| Magnesium stearate | 0.4 |

Example C

Tablet

| Ingredient | Weight % (by weight of total composition) |
| --- | --- |
| Acolbifene | 5.0 |
| DHEA | 15.0 |
| Gelatin | 5.0 |
| Lactose | 58.5 |
| Starch | 16.5 |

Example D

Gelatin Capsule

| Ingredient | Weight % (by weight of total composition) |
| --- | --- |
| Acolbifene | 5.0 |
| DHEA | 15.0 |
| Lactose hydrous | 65.0 |
| Starch | 4.8 |
| Cellulose microcrystalline | 9.8 |
| Magnesium stearate | 0.4 |

Example E

Tablet

| Ingredient | Weight % (by weight of total composition) |
| --- | --- |
| Acolbifene | 5.0 |
| DHEA | 15.0 |
| Premarin | 0.5 |
| Gelatin | 5.0 |
| Lactose | 63.0 |
| Starch | 16.5 |

Example F

Gelatin Capsule

| Ingredient | Weight % (by weight of total composition) |
| --- | --- |
| Acolbifene | 5.0 |
| DHEA | 15.0 |
| Premarin | 0.5 |
| Lactose hydrous | 64.5 |

Example G

Tablet

| Ingredient | Weight % (by weight of total composition) |
|---|---|
| Starch | 4.8 |
| Cellulose microcrystalline | 9.8 |
| Magnesium stearate | 0.4 |

| Ingredient | Weight % (by weight of total composition) |
|---|---|
| Sildenafil | 15.0 |
| DHEA | 15.0 |
| Gelatin | 5.0 |
| Lactose | 48.5 |
| Starch | 16.5 |

Example H

Gelatin Capsule

| Ingredient | Weight % (by weight of total composition) |
|---|---|
| Sildenafil | 15.0 |
| Acolbifene | 5.0 |
| DHEA | 15.0 |
| Lactose hydrous | 50.0 |
| Starch | 4.8 |
| Cellulose microcrystalline | 9.8 |
| Magnesium stearate | 0.4 |

Example I

Tablet

| Ingredient | Weight % (by weight of total composition) |
|---|---|
| Acolbifene | 5.0 |
| DHEA | 15.0 |
| Sildenafil | 15.0 |
| Gelatin | 5.0 |
| Lactose | 43.5 |
| Starch | 16.5 |

Example J

Gelatin Capsule

| Ingredient | Weight % (by weight of total composition) |
|---|---|
| Acolbifene | 5.0 |
| DHEA | 15.0 |
| Sildenafil | 15.0 |
| Lactose hydrous | 50.0 |
| Starch | 4.8 |
| Cellulose microcrystalline | 9.8 |
| Magnesium stearate | 0.4 |

Example K

Vaginal Cream

| Ingredient | Weight % (by weight of total composition) |
|---|---|
| DHEA | 1.0 |
| Acolbifene | 0.2 |
| Emulsifying Wax, NF | 18.0 |
| Light mineral oil, NF | 12.0 |
| Benzyl alcohol | 1.0 |
| Ethanol 95% USP | 33.8 |
| Purifed water, USP | 34.0 |

Example L

Vaginal Suppository

| Ingredient | Weight % (by weight of total composition) |
|---|---|
| DHEA | 0.66 to 2.0 |
| Whitepsol H-15 base | 98 to 99.34 |

DHEA suppositories were prepared using Whitepsol H-15 base (Medisca, Montreal, Canada). Any other lipophilic base such as Fattibase, Wecobee, cocoa butter, theobroma oil or other combinations of Whitepsol bases could used.

Kit Examples

Set forth below, by way of example and not of limitation, are several kits utilizing preferred active SREM Acolbifene, preferred active a sex steroid precursor DHEA, preferred estrogens 17β-estradiol or conjugated estrogens, preferred type 5 cGMP phosphodiesterase inhibitor Sildenafil or Tadalafil. The concentration of active ingredient may be varied over a wide range as discussed herein. The amounts and types of other ingredients that may be included are well known in the art.

Example A

The SERM, estrogens and type 5 cGMP phosphodiesterase inhibitor are orally administered while the sex steroid precursor is applied locally or percutaneously administered.

SERM Composition for Oral Administration (Capsules)

| Ingredient | Weight % (by weight of total composition) |
|---|---|
| Acolbifene | 5.0 |
| Lactose hydrous | 80.0 |
| Starch | 4.8 |
| Cellulose microcrystalline | 9.8 |
| Magnesium stearate | 0.4 |

SERM+Estrogens Composition for Oral Administration (Capsules)

| Ingredient | Weight % (by weight of total composition) |
|---|---|
| Acolbifene | 5.0 |
| Premarin | 0.5 |
| Lactose hydrous | 79.5 |
| Starch | 4.8 |
| Cellulose microcrystalline | 9.8 |
| Magnesium stearate | 0.4 |

SERM+Estrogens+Type 5 cGMP Phosphodiesterase Inhibitor Composition for Oral Administration (Capsules)

| Ingredient | Weight % (by weight of total composition) |
|---|---|
| Acolbifene | 5.0 |
| Premarin | 0.5 |
| Sildenafil | 15.0 |
| Lactose hydrous | 64.5 |
| Starch | 4.8 |
| Cellulose microcrystalline | 9.8 |
| Magnesium stearate | 0.4 |

Sex Steroid Precursor Composition for Topical Administration (Gel)

| Ingredient | Weight % (by weight of total composition) |
|---|---|
| DHEA | 2.0 |
| Caprylic-capric Triglyceride (Neobee M-5) | 5.0 |
| Hexylene Glycol | 15.0 |
| Transcutol (diethyleneglycol monomethyl ether) | 5.0 |
| Benzyl alcohol | 2.0 |
| Cyclomethicone (Dow corning 345) | 5.0 |
| Ethanol (absolute) | 64.0 |
| Hydroxypropylcellulose (1500 cps) (KLUCEL) | 2.0 |

Example B

The SERM and the sex steroid precursor are orally administered.

Non-Steroidal Antiestrogen Composition for Oral Administration (Capsules)

| Ingredient | Weight % (by weight of total composition) |
|---|---|
| Acolbifene | 5.0 |
| Lactose hydrous | 80.0 |
| Starch | 4.8 |
| Cellulose microcrystalline | 9.8 |
| Magnesium stearate | 0.4 |

Sex Steroid Precursor Composition for Oral Administration (Gelatin Capsule)

| Ingredient | Weight % (by weight of total composition) |
|---|---|
| DHEA | 15.0 |
| Lactose hydrous | 70.0 |
| Starch | 4.8 |
| Cellulose microcrystalline | 9.8 |
| Magnesium stearate | 0.4 |

Other SERMs (Toremifene, Ospemifene, Raloxifene, Arzoxifene, Lasofoxifene, TSE-424, ERA-923, EM-800, SERM 3339, GW-5638) may be substituted for Acolbifene in the above formulations, as well as other sex steroid inhibitors may be substituted for DHEA, other estrogens may be substituted for Premarin and other type 5 cGMP phosphodiesterase inhibitor may be substituted for Sildenafil or Tadalafil or by prostaglandin E1. More than one SERM or more than one precursor or estrogens or type 5 cGMP phosphodiesterase inhibitor may be included in which case the combined weight percentage is preferably that of the weight percentage for the single precursor or single SERM given in the examples above.

The invention has been described in terms of preferred embodiments and examples, but is not limited thereby. Those of skill in the art will readily recognize the broader applicability and scope of the invention which is limited only by the patent claims herein.

What is claimed is:

1. A method of treating or reducing the likelihood of acquiring a vaginal disease or condition caused by the atrophy of either or both of the layer lamina propria and/or the layer muscularis of the vagina in postmenopausal women, wherein said disease or condition is sexual dysfunction other than dyspareunia, said method comprising administering a sex steroid precursor that is dehydroepiandrosterone, to a patient in need of said treatment and also administering to said patient, as part of a combination therapy, a selective estrogen receptor modulator that is:

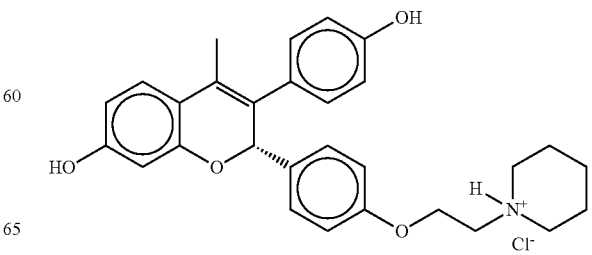

2. The method of claim 1, wherein the sex steroid precursor is administered intravaginally.

3. The method of claim 1, wherein the sex steroid precursor is orally or percutaneously administered.

4. The method of claim 1 wherein the selective estrogen receptor modulator is orally, percutaneously or intravaginally administered.

\* \* \* \* \*